(12) United States Patent
Zhang

(10) Patent No.: US 10,745,410 B2
(45) Date of Patent: Aug. 18, 2020

(54) SUBSTITUTED [5,6]CYCLIC-4(3H)-PYRIMIDINONES AS ANTICANCER AGENTS

(71) Applicant: ZENJI RESEARCH LABORATORIES, Nanjing, Jiangsu (CN)

(72) Inventor: Hai-Jun Zhang, Boxborough, MA (US)

(73) Assignee: ZENJI RESEARCH LABORATORIES, Nanjing (CN)

( * ) Notice: Subject to any disclaimer, the term of this patent is extended or adjusted under 35 U.S.C. 154(b) by 0 days.

(21) Appl. No.: 16/487,832

(22) PCT Filed: May 8, 2018

(86) PCT No.: PCT/US2018/031474
§ 371 (c)(1),
(2) Date: Aug. 22, 2019

(87) PCT Pub. No.: WO2018/217439
PCT Pub. Date: Nov. 29, 2018

(65) Prior Publication Data
US 2020/0055867 A1    Feb. 20, 2020

Related U.S. Application Data

(60) Provisional application No. 62/509,128, filed on May 21, 2017.

(51) Int. Cl.
*C07D 495/04* (2006.01)
*A61K 31/519* (2006.01)

(52) U.S. Cl.
CPC ................. *C07D 495/04* (2013.01)

(58) Field of Classification Search
None
See application file for complete search history.

(56) References Cited

U.S. PATENT DOCUMENTS

2009/0030196 A1   1/2009   Wang et al.
2016/0310494 A1  10/2016   Homma et al.

OTHER PUBLICATIONS

Yaowu, Twelfth Five-Year Plan. Textbook for Pharmaceutical Majors: Medicinal Chemistry, 2nd Edition. Henan Science and Technology Press. Ma Ying (Ed.). pp. 5-8, (2012).
Internation Search Report and Written Opinion for PCT/US12018/31474, dated Aug. 30, 2019, pp. 1-11.

*Primary Examiner* — Samantha L Shterengarts
(74) *Attorney, Agent, or Firm* — McCarter & English, LLP; Steven G. Davis; Wei Song

(57) ABSTRACT

The present invention relates to novel substituted [5,6] cyclic-4(3H)-pyrimidinone compounds of formula (I) and their preparation methods. (I) In particular, the present invention relates to novel substituted [5,6]cyclic-4(3H)-pyrimidinone compounds useful as inhibitors of protein kinases, specifically CDC7 (cell division cycle 7) inhibitors.

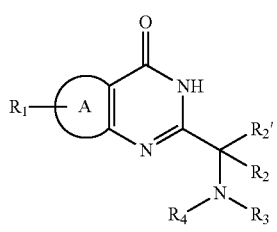

(I)

8 Claims, No Drawings

SUBSTITUTED [5,6]CYCLIC-4(3H)-PYRIMIDINONES AS ANTICANCER AGENTS

CROSS-REFERENCE TO RELATED APPLICATIONS

This application is a U.S. national stage filing, under 35 U.S.C. § 371(c), of International Application No. PCT/US2018/031474, filed on May 8, 2018, which claims the benefit of U.S. Provisional Application No. 62/509,128, filed on May 21, 2017. The entire teachings of the aforementioned applications are incorporated herein by reference.

TECHNICAL FIELD

The present invention relates to novel substituted [5,6] cyclic-4(3H)-pyrimidinone compounds and their preparation methods. In particular, the present invention relates to novel substituted [5,6]cyclic-4(3H)-pyrimidinone compounds useful as inhibitors of protein kinases, specifically CDC7 (cell division cycle 7) inhibitors.

BACKGROUND OF THE INVENTION

CDC7 (cell division cycle 7) is a serine-threonline kinase that plays a critical role in DNA synthesis and is required for the activation of DNA replication origins throughout the S phase of the cell cycle. Inhibition of CDC7 in cancer causes lethal S phase and M phase progression, whereas normal cells survive, mostly likely through induction of cell cycle arrest at the DNA replication checkpoint. It has been reported in the literature that CDC7 is over expressed in many cancers, including triple-negative breast cancer, which is a still highly unmet medical need.[1,2,3,4,5].

Among many small molecule CDC 7 inhibitors in the discovery stage and early clinic stage, Exelixis and Takeda separately patented a class of molecules that contains a [5,6]cyclic-4(3H)-pyrimidinone core structure.[6,7,8].

REFERENCES

1. Elena S. Koltun, et al. *Bioorg. & Med. Chem. Lett.* 2012, 22, 3727-3731, and references cited in this paper.
2. *Genes Dev.* 2010, 24, 1208-1219.
3. *Neoplasia*. 2008, 10(9), 920-931.
4. *Clin. Cancer Res.* 2010, 16, 4503-4508.
5. *Nature Chem. Bio.* 2008, 4, 357-365.
6. Benzofuropyrimidinones as protein kinase inhibitors. PCT Int. Appl. (2009), WO 2009/086264 A1.
7. Preparation of (pyrazol-4-yl)dihydrothienopyrimidinones as anticancer agents. PCT Int. Appl. (2011), WO 2011102399 A1 20110825.
8. US20130029969 Heterocyclic Compound

DESCRIPTION OF THE INVENTION

The present invention provides novel substituted [5,6] cyclo-4(3H)-pyrimidinone compounds and stable pharmaceutically acceptable compositions comprising them. These compounds are CDC7 inhibitors and are useful in treatment of diseases, such as cancers, that are related to CDC7 inhibition mechanism.

In one aspect, the invention provides compounds of the general formula (I), or a pharmaceutically acceptable salt or thereof, wherein:

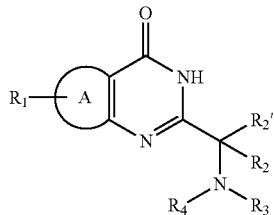

(I)

The ring size for A ring in formula (I) is 5 or 6;
A ring may have one or multiple heteroatoms, for example but not limited to N, O or S;
$R_1$ represents an aromatic or non-aromatic substitution group;
$R_1$ can be at any possible position on A ring;
There may be two $R_1$ groups, same or different, on A ring;
$R_1$ may have one or multiple heteroatoms, for example but not limited to F, Cl, N, O or S;
When $R_1$ contains an aromatic ring, the aromatic ring may have one or multiple heteroatoms on the ring, for example but not limited to N, O or S;
$R_2$ represents an aliphatic substitution group with C1-20 hydrocarbons or H;
$R_2'$ represents an aliphatic substitution group with C1-20 hydrocarbons or H;
$R_2$ and $R_2'$ can be the same or different;
A chiral center is contained on the C atom attaching to $R_2$ and $R_2'$ when $R_2$ is different from $R_2'$, including when $R_2$ or $R_2'$ is a H atom; the configuration of the chiral center can be either (S) or (R);
$R_3$ represents an aliphatic substitution group with C1-20 hydrocarbons or H;
$R_4$ represents an aliphatic substitution group with C1-20 hydrocarbons or H;
$R_2$, $R_2'$, $R_3$ and $R_4$ may have one or multiple heteroatoms, for example but not limited to F, Cl, N, O or S;
$R_2$ and $R_2'$ can be connected to form a 3 to 8 membered ring;
$R_3$ and $R_4$ can be connected to form a 3 to 8 membered ring;
$R_2$ or $R_2'$ can be connected to $R_3$ to form a 3 to 8 membered ring;
$R_2$ or $R_2'$ can be connected to $R_4$ to form a 3 to 8 membered ring.

In another aspect, the invention provides compounds of the general formula (II), or a pharmaceutically acceptable salt or thereof, wherein:

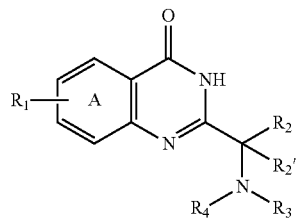

(II)

$R_1$ represents an aromatic or non-aromatic substitution group;
$R_1$ can be at any possible position on A ring;

There may be two $R_1$ groups, same or different, on A ring;

$R_1$ may have one or multiple heteroatoms, for example but not limited to F, Cl, N, O or S;

When $R_1$ contains an aromatic ring, the aromatic ring may have one or multiple heteroatoms on the ring, for example but not limited to N, O or S;

$R_2$ represents an aliphatic substitution group with C1-20 hydrocarbons or H;

$R_2'$ represents an aliphatic substitution group with C1-20 hydrocarbons or H;

$R_2$ and $R_2'$ can be the same or different;

A chiral center is contained on the C atom attaching to $R_2$ and $R_2'$ when $R_2$ is different from $R_2'$, including when $R_2$ or $R_2'$ is a H atom; the configuration of the chiral center can be either (S) or (R);

$R_3$ represents an aliphatic substitution group with C1-20 hydrocarbons or H;

$R_4$ represents an aliphatic substitution group with C1-20 hydrocarbons or H;

$R_2$, $R_2'$, $R_3$ and $R_4$ may have one or multiple heteroatoms, for example but not limited to F, Cl, N, O or S;

$R_2$ and $R_2'$ can be connected to form a 3 to 8 membered ring;

$R_3$ and $R_4$ can be connected to form a 3 to 8 membered ring;

$R_2$ or $R_2'$ can be connected to $R_3$ to form a 3 to 8 membered ring;

$R_2$ or $R_2'$ can be connected to $R_4$ to form a 3 to 8 membered ring.

In another aspect, the invention provides compounds of the general formula (III), or a pharmaceutically acceptable salt or thereof, wherein:

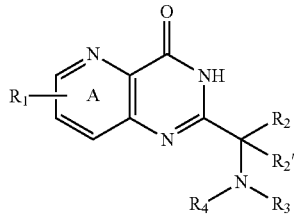

(III)

$R_1$ represents an aromatic or non-aromatic substitution group;

$R_1$ can be at any possible position on A ring;

There may be two $R_1$ groups, same or different, on A ring;

$R_1$ may have one or multiple heteroatoms, for example but not limited to F, Cl, N, O or S;

When $R_1$ contains an aromatic ring, the aromatic ring may have one or multiple heteroatoms on the ring, for example but not limited to N, O or S;

$R_2$ represents an aliphatic substitution group with C1-20 hydrocarbons or H;

$R_2'$ represents an aliphatic substitution group with C1-20 hydrocarbons or H;

$R_2$ and $R_2'$ can be the same or different;

A chiral center is contained on the C atom attaching to $R_2$ and $R_2'$ when $R_2$ is different from $R_2'$, including when $R_2$ or $R_2'$ is a H atom; the configuration of the chiral center can be either (S) or (R);

$R_3$ represents an aliphatic substitution group with C1-20 hydrocarbons or H;

$R_4$ represents an aliphatic substitution group with C1-20 hydrocarbons or H;

$R_2$, $R_2'$, $R_3$ and $R_4$ may have one or multiple heteroatoms, for example but not limited to F, Cl, N, O or S;

$R_2$ and $R_2'$ can be connected to form a 3 to 8 membered ring;

$R_3$ and $R_4$ can be connected to form a 3 to 8 membered ring;

$R_2$ or $R_2'$ can be connected to $R_3$ to form a 3 to 8 membered ring;

$R_2$ or $R_2'$ can be connected to $R_4$ to form a 3 to 8 membered ring.

In another aspect, the invention provides compounds of the general formula (IV): or a pharmaceutically acceptable salt or thereof, wherein:

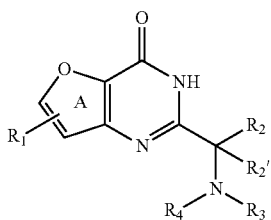

(IV)

$R_1$ represents an aromatic or non-aromatic substitution group;

$R_1$ can be at any possible position on A ring;

There may be two $R_1$ groups, same or different, on A ring;

$R_1$ may have one or multiple heteroatoms, for example but not limited to F, Cl, N, O or S;

When $R_1$ contains an aromatic ring, the aromatic ring may have one or multiple heteroatoms on the ring, for example but not limited to N, O or S;

$R_2$ represents an aliphatic substitution group with C1-20 hydrocarbons or H;

$R_2'$ represents an aliphatic substitution group with C1-20 hydrocarbons or H;

$R_2$ and $R_2'$ can be the same or different;

A chiral center is contained on the C atom attaching to $R_2$ and $R_2'$ when $R_2$ is different from $R_2'$, including when $R_2$ or $R_2'$ is a H atom; the configuration of the chiral center can be either (S) or (R);

$R_3$ represents an aliphatic substitution group with C1-20 hydrocarbons or H;

$R_4$ represents an aliphatic substitution group with C1-20 hydrocarbons or H;

$R_2$, $R_2'$, $R_3$ and $R_4$ may have one or multiple heteroatoms, for example but not limited to F, Cl, N, O or S;

$R_2$ and $R_2'$ can be connected to form a 3 to 8 membered ring;

$R_3$ and $R_4$ can be connected to form a 3 to 8 membered ring;

$R_2$ or $R_2'$ can be connected to $R_3$ to form a 3 to 8 membered ring;

$R_2$ or $R_2'$ can be connected to $R_4$ to form a 3 to 8 membered ring.

In another aspect, the invention provides a compound of the formula (V), or a pharmaceutically acceptable salt or thereof, wherein:

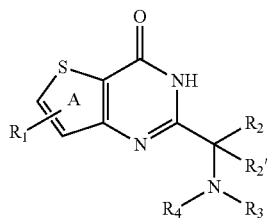

(V)

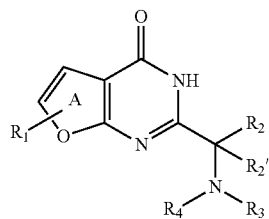

(VI)

R$_1$ represents an aromatic or non-aromatic substitution group, for example and not limited to, phenyl, pyridyl, pyrimidyl, pyrazol, pyrimidinyl;

R$_1$ can be at any possible position on A ring;

There may be two R$_1$ groups, same or different, on A ring;

R$_1$ may have one or multiple heteroatoms, for example but not limited to F, Cl, N, O or S;

When R$_1$ contains an aromatic ring, the aromatic ring may have one or multiple heteroatoms on the ring, for example but not limited to N, O or S;

When R$_1$ contains an aromatic ring, the aromatic ring may be substituted by C1-6 hydrocarbon group, for example and not limited to, Me, Et, CF$_3$;

R$_2$ represents an aliphatic substitution group with C1-20 hydrocarbons or H, for example and not limited to, Me, Et, iPr, Pr, cycle Pr;

R$_2$' represents an aliphatic substitution group with C1-20 hydrocarbons or H, for example and not limited to, Me, Et, iPr, Pr, cycle Pr;

R$_2$ and R$_2$' can be the same or different;

A chiral center is contained on the C atom attaching to R$_2$ and R$_2$' when R$_2$ is different from R$_2$', including when R$_2$ or R$_2$' is a H atom; the configuration of the chiral center can be either (S) or (R);

R$_3$ represents an aliphatic substitution group with C1-20 hydrocarbons or H;

R$_4$ represents an aliphatic substitution group with C1-20 hydrocarbons or H;

R$_2$, R$_2$', R$_3$ and R$_4$ may have one or multiple heteroatoms, for example but not limited to F, Cl, N, O or S;

R$_2$ and R$_2$' can be connected to form a 3 to 8 membered ring;

R$_3$ and R$_4$ can be connected to form a 3 to 8 membered ring;

R$_2$ or R$_2$' can be connected to R$_3$ to form a 3 to 8 membered ring;

R$_2$ or R$_2$' can be connected to R$_4$ to form a 3 to 8 membered ring.

In one embodiment, the invention provides a compound of the formula (V), or a pharmaceutically acceptable salt or thereof, wherein R$_1$ is one of the following substitution group, phenyl, pyridyl, pyrimidyl, pyrazol, pyrimidinyl.

In one embodiment, R$_1$ may have one or multiple heteroatom substitutions, for example but not limited to F, Cl.

In one embodiment, wherein R$_1$ may have one or more C1-6 hydrocarbon group, for example and not limited to, Me, Et, CF$_3$.

In one embodiment, wherein R$_2$ is one of the following substitution groups, Me, Et, iPr, Pr, cyclol Pr, and R$_2$' is H. Both enantiomers are claimed.

In one embodiment, wherein R$_3$ and R$_4$ are both H.

In another aspect, the invention provides a compound of the formula (VI), or a pharmaceutically acceptable salt or thereof, wherein:

R$_1$ represents an aromatic or non-aromatic substitution group;

R$_1$ can be at any possible position on A ring;

There may be two R$_1$ groups, same or different, on A ring;

R$_1$ may have one or multiple heteroatoms, for example but not limited to F, Cl, N, O or S;

When R$_1$ contains an aromatic ring, the aromatic ring may have one or multiple heteroatoms on the ring, for example but not limited to N, O or S;

R$_2$ represents an aliphatic substitution group with C1-20 hydrocarbons or H;

R$_2$' represents an aliphatic substitution group with C1-20 hydrocarbons or H;

R$_2$ and R$_2$' can be the same or different;

A chiral center is contained on the C atom attaching to R$_2$ and R$_2$' when R$_2$ is different from R$_2$', including when R$_2$ or R$_2$' is a H atom; the configuration of the chiral center can be either (S) or (R);

R$_3$ represents an aliphatic substitution group with C1-20 hydrocarbons or H;

R$_4$ represents an aliphatic substitution group with C1-20 hydrocarbons or H;

R$_2$, R$_2$', R$_3$ and R$_4$ may have one or multiple heteroatoms, for example but not limited to F, Cl, N, O or S;

R$_2$ and R$_2$' can be connected to form a 3 to 8 membered ring;

R$_3$ and R$_4$ can be connected to form a 3 to 8 membered ring;

R$_2$ or R$_2$' can be connected to R$_3$ to form a 3 to 8 membered ring;

R$_2$ or R$_2$' can be connected to R$_4$ to form a 3 to 8 membered ring.

In another aspect, the invention provides a compound of the formula (VII), or a pharmaceutically acceptable salt or thereof, wherein:

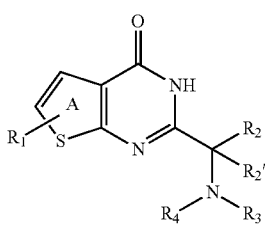

(VII)

R$_1$ represents an aromatic or non-aromatic substitution group;

R$_1$ can be at any possible position on A ring;

There may be two R$_1$ groups, same or different, on A ring;

R$_1$ may have one or multiple heteroatoms, for example but not limited to F, Cl, N, O or S;

When R$_1$ contains an aromatic ring, the aromatic ring may have one or multiple heteroatoms on the ring, for example but not limited to N, O or S;

$R_2$ represents an aliphatic substitution group with C1-20 hydrocarbons or H;

$R_2'$ represents an aliphatic substitution group with C1-20 hydrocarbons or H;

$R_2$ and $R_2'$ can be the same or different;

A chiral center is contained on the C atom attaching to $R_2$ and $R_2'$ when $R_2$ is different from $R_2'$, including when $R_2$ or $R_2'$ is a H atom; the configuration of the chiral center can be either (S) or (R);

$R_3$ represents an aliphatic substitution group with C1-20 hydrocarbons or H;

$R_4$ represents an aliphatic substitution group with C1-20 hydrocarbons or H;

$R_2$, $R_2'$, $R_3$ and $R_4$ may have one or multiple heteroatoms, for example but not limited to F, Cl, N, O or S;

$R_2$ and $R_2'$ can be connected to form a 3 to 8 membered ring;

$R_3$ and $R_4$ can be connected to form a 3 to 8 membered ring;

$R_2$ or $R_2'$ can be connected to $R_3$ to form a 3 to 8 membered ring;

$R_2$ or $R_2'$ can be connected to $R_4$ to form a 3 to 8 membered ring.

The term "pharmaceutically acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.*, 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as acetic acid, benzenesulfonic, benzoic, ethanesulfonic, methanesulfonic, succinic, and trifluoroacetic acid acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

The term "pharmaceutically acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.*, 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as acetic acid, benzenesulfonic, benzoic, ethanesulfonic, methanesulfonic, succinic, and trifluoroacetic acid acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

If a group is described as being "substituted," a non-hydrogen substituent replaces a hydrogen on a carbon or nitrogen of the substituent. Thus, for example, a substituted alkyl is an alkyl wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent can be identical or different (unless otherwise stated). As used herein, many moieties (e.g., alkyl, alkylene, cycloalkyl, cycloalkylene, aryl, arylene, heteroaryl, heteroarylene, heterocyclyl or heterocyclylene) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. If more than one substituent is present, then each substituent is independently selected. Such means for substitution are well-known in the art and/or taught by the instant disclosure. The optional substituents can be any substituents that are suitable to attach to the moiety. A person of ordinary skill in the art will recognize that the compounds and definitions provided do not include impermissible substituent patterns (e.g., methyl substituted with 5 different groups, and the like). Such impermissible substitution patterns are clearly recognized by a person of ordinary skill in the art.

Suitable substituents are those which do not have a significant adverse effect on the ability of the compound to inhibit CDC7. Where suitable substituents are not specifically enumerated, exemplary substituents include, but are not limited to: halo, —CN, alkyl, alkoxy, halomethyl, halomethoxy, $(C_1-C_5)$alkyl, halo$(C_1-C_5)$alkyl, $(C_1-C_5)$alkoxy, —NO$_2$, —OR$^{c'}$—NR$^{a'}$R$^{b'}$, —S(O)$_i$R$^{a'}$, —NR$^{a'}$S(O)$_i$R$^{b'}$, —S(O)$_i$NR$^{a'}$R$^{b'}$, —C(=O)OR$^{a'}$, —OC(=O)OR$^{a'}$, —C(=S)OR$^{a'}$, —O(C=S)R$^{a'}$, —C(=O)NR$^{a'}$R$^{b'}$, —NR$^{a'}$C(=O)R$^{b'}$, —C(=S)NR$^{a'}$R$^{b'}$, —NR$^{a'}$C(=S)R$^{b'}$, NR$^{a'}$(C=O)OR$^{b'}$, —O(C=O)NR$^{a'}$R$^{b'}$, —NR$^{a'}$(C=S)OR$^{b'}$, —O(C=S)NR$^{a'}$R$^{b'}$, —NR$^{a'}$(C=O)NR$^{a'}$R$^{b'}$, NR$^{a'}$(C=S)NR$^{a'}$R$^{b'}$, —C(=S)R$^{a'}$, —C(=O)R$^{a'}$, $(C_3-C_6)$cycloalkyl, monocyclic heteroaryl and phenyl, wherein the $(C_3-C_6)$ cycloalkyl, monocyclic heteroaryl and phenyl substituents are optionally and independently substituted with —CH$_3$, halomethyl, halo, methoxy or halomethoxy. Each R$^{a'}$ and each R$^{b'}$ are independently selected from —H and $(C_1-C_5)$ alkyl, wherein the $(C_1-C_5)$alkyl group represented by R$^{a'}$ or R$^{b'}$ is optionally substituted with hydroxyl or $(C_1-C_3)$ alkoxy; R$^{c'}$ is —H, halo$(C_1-C_5)$alkyl or $(C_1-C_5)$alkyl, wherein the $(C_1-C_5)$alkyl group represented by R$^{c'}$ is optionally substituted with hydroxyl or $(C_1-C_3)$alkoxy; and i is 0, 1, or 2. =O is also a suitable substituent for alkyl, cycloalkyl, cycloalkenyl and hetercyclyl.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof. The term "geometric isomer" refers to compounds having at least one double bond, wherein the double bond(s) may exist in cis (also referred to as syn or entgegen (E)) or trans (also referred to as anti or zusammen (Z)) forms as well as mixtures thereof. When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Pharmaceutical Compositions

The compounds disclosed therein are CDC7 inhibitors. The pharmaceutical composition of the present invention comprises one or more CDC7 inhibitors, or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

The present invention provides a method of treating a subject with a disease which can be ameliorated by inhibition of CDC7, by administering to the subject an effective amount of one or more disclosed compounds, or a pharmaceutically acceptable salt thereof, or the corresponding pharmaceutical composition.

The present invention also provides a method of treating cancer, by administering to the subject in need thereof an effective amount of one or more disclosed compounds, or a pharmaceutically acceptable salt thereof, or the pharmaceutical composition thereof.

Another embodiment is a method of treating a cancer selected from the group consisting of colon cancer, ovarian cancer and pancreatic cancer.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In certain embodiments, the invention provides methods for using the compounds of the invention, or the pharmaceutically acceptable salts, or the pharmaceutical compositions thereof. The compounds of the invention, or the pharmaceutically acceptable salts, or the pharmaceutical compositions thereof may be useful for a variety of therapeutic applications including treating and/or reducing a wide variety of diseases and disorders including, for example, cancer. The methods comprise administering to a subject in need thereof an effective amount of one or more compounds of the invention, or a pharmaceutically acceptable salt thereof, or the pharmaceutical compositions thereof.

Methods of Administration and Dosage Forms

The precise amount of compound administered to provide an "effective amount" to the subject will depend on the mode of administration, the type, and severity of the disease, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used by following, for example, dosages reported in the literature and recommended in the *Physician's Desk Reference* (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a CDC7 mediated disease using the disclosed CDC7 inhibitors for guidance.

The compounds or the corresponding pharmaceutical compositions taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

EXAMPLES AND METHODS

Biochemical Assay Method

N-terminal GST-tagged CDC7 and DBF4 full-length proteins were co-expressed by baculovirus insect expression (BV) system and purified by GST affinity column. Used MCM2 protein as substrate, N-terminal His tag MCM2 was expressed by *E. coli* and purified by His affinity column.

Biochemical assay was tested in the U-shaped bottom 384 plate (corning, #4514) with a final volume of 20 ul at 27° C. The concentration of CDC7 was optimized by the enzyme titration experiment. CDC7 kinase was diluted in assay buffer (40 mM Tris.HCl pH 7.25, 100 ug/mL BSA, and 20 mM $MgCl_2$) to get 2.4× enzyme solutions. Compounds were dissolved in 10 mM DMSO, and series diluted in DMSO from 0.3 mM to 0.3 nM (5 concentration pts); All dilutions were diluted 30× in assay buffer to get 6× compounds solutions. MCM2 Substrate and ATP were diluted to 2.4× mixed solution. Add 2 ul test compound solution to 384 assay plate, then add 5 ul substrate/ATP mixed solution, at last add 5 ul enzyme solution, incubate at 27° C. for 180 mins. Transfer 5 ul reaction solution to another 384 assay plate, then add 5 ul ADP-Glo™ Reagent (Promega) to each well and incubate at 27° C. for 40 mins; Add 10 ul Kinase Detection Reagent (Promega) to each well and incubate at 27° C. for 30 mins. 10 uM CDC7-3 compound was used as 100% inhibition while 100% DMSO control was used as 0% inhibition. Each test has three replications at least.

The final concentration of the reagents: ATP was 500 uM; MCM2 was 400 ug/ml; CDC7/DBF4 was 200 nM. The data were obtained by TECAN F200 and calculated by GraphPad Prism 5.0; IC$_{50}$ values were adjusted by Dose-response-Inhibition-Variable slope model.

Proliferation experiment in COLO 205 cell line

Tissue Culture.

Cells were maintained in 10% FBS (Gibco #10099141)/RPMI 1640 (Gibco # A10491). The cells were harvested with 0.25% Trypsin/EDTA (Amresco #9002077), re-suspended in 10% FBS/RPMI 1640 and plated at 8,000 cells per well in 90 ul of media in a 96-well black plate with clear bottoms (Corning #3603). The cells were allowed to incubate overnight in a 37° C., 5% CO$_2$ humidified tissue culture incubator. A 10-point test compound curve was prepared by serial diluting a 10 mM stock 1:3 in DMSO in a 384-well compound plate (costar #3656). The serial diluted compounds were transferred to the plate containing medium for further dilution. The final concentration was from 10 uM to 0.000508 uM. The serial diluted compounds were transferred to the plate containing cells by using a volley (RAININ) and the cells were placed back in the incubator for 72 hours. Luminescent detection was carried out with CellTiter-Glo® Luminescent Cell Viability Assay (promega # G7572). Signal was read on TECAN Infinite F200.

Examples of compounds within formula V.

| Structure | Code | IUPAC name | CDC7 enzyme IC$_{50}$ (nm) A = < 0.1 µM B = < 1 µM C = < 10 µM D = > 10 µM | Colo 205 cell GI$_{50}$ (nm) A = < 0.1 µM B = < 1 µM C = < 10 µM D = > 10 µM |
|---|---|---|---|---|
| 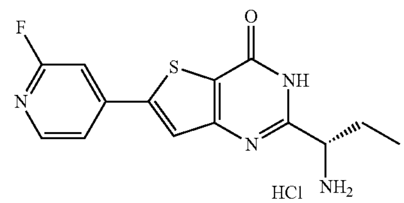 [SMILES: CC[C@H](N)c1nc2cc(-c3ccnc(F)c3)sc2c(=O)[nH]1 ; Cl] | 13a | (S)-2-(1-aminopropyl)-6-(2-fluoropyridin-4-yl)thieno[3,2-d]pyrimidin-4(3H)-one hydrochloride | B | B |
| 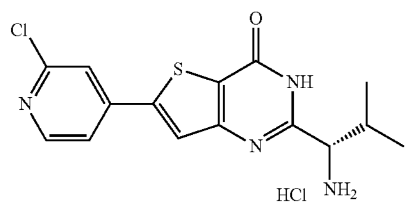 [SMILES: CC(C)[C@H](N)c1nc2cc(-c3ccnc(Cl)c3)sc2c(=O)[nH]1 ; Cl] | 7a | (S)-2-(1-amino-2-methylpropyl)-6-(2-chloropyridin-4-yl)thieno[3,2-d]pyrimidin-4(3H)-one hydrochloride | B | C |
| 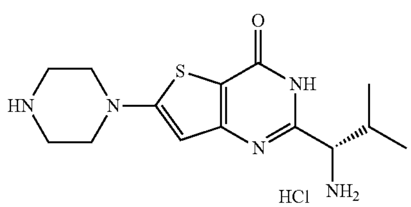 [SMILES: CC(C)[C@H](N)c1nc2cc(N3CCNCC3)sc2c(=O)[nH]1 ; Cl] | 67 | (S)-2-(1-amino-2-methylpropyl)-6-(piperazin-1-yl)thieno[3,2-d]pyrimidin-4(3H)-one hydrochloride | C | D |
| 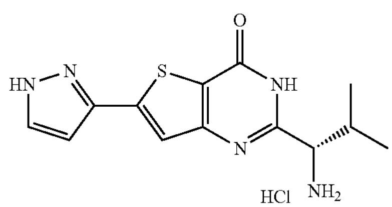 [SMILES: CC(C)[C@H](N)c1nc2cc(-c3cc[nH]n3)sc2c(=O)[nH]1 ; Cl] | 7c | (S)-2-(1-amino-2-methylpropyl)-6-(1H-pyrazol-3-yl)thieno[3,2-d]pyrimidin-4(3H)-one hydrochloride | C | D |
| 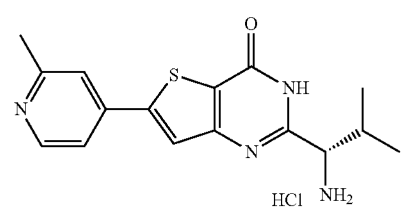 [SMILES: Cc1cc(-c2cc3nc([C@@H](N)C(C)C)[nH]c(=O)c3s2)ccn1 ; Cl] | 7b | (S)-2-(1-amino-2-methylpropyl)-6-(2-methylpyridin-4-yl)thieno[3,2-d]pyrimidin-4(3H)-one hydrochloride | B | C |

-continued

| Structure | Code | IUPAC name | CDC7 enzyme IC$_{50}$ (nm) A = < 0.1 μM B = < 1 μM C = < 10 μM D = > 10 μM | Colo 205 cell GI$_{50}$ (nm) A = < 0.1 μM B = < 1 μM C = < 10 μM D = > 10 μM |
|---|---|---|---|---|
| 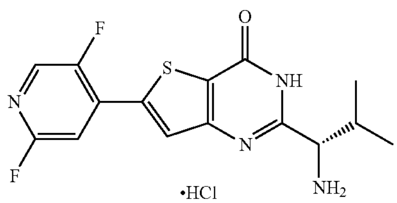 [SMILES: CC(C)[C@H](N)c1nc2cc(-c3cc(F)ncc3F)sc2c(=O)[nH]1 ; Cl] | 7d | (S)-2-(1-amino-2-methylpropyl)-6-(2,5-difluoropyridin-4-yl)thieno[3,2-d]pyrimidin-4(3H)-one hydrochloride | B | B |
| 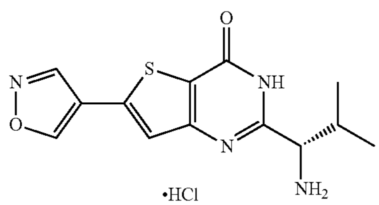 [SMILES: CC(C)[C@H](N)c1nc2cc(-c3cnoc3)sc2c(=O)[nH]1 ; Cl] | 7e | (S)-2-(1-amino-2-methylpropyl)-6-(isoxazol-4-yl)thieno[3,2-d]pyrimidin-4(3H)-one hydrochloride | D | D |
| 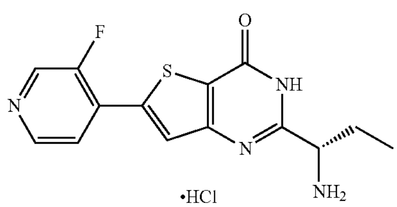 [SMILES: CC[C@H](N)c1nc2cc(-c3ccncc3F)sc2c(=O)[nH]1 ; Cl] | 13b | (S)-2-(1-aminopropyl)-6-(3-fluoropyridin-4-yl)thieno[3,2-d]pyrimidin-4(3H)-one hydrochloride | A | A |
| 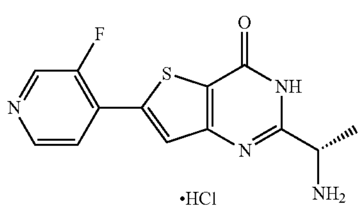 [SMILES: C[C@H](N)c1nc2cc(-c3ccncc3F)sc2c(=O)[nH]1 ; Cl] | 21 | (S)-2-(1-aminoethyl)-6-(3-fluoropyridin-4-yl)thieno[3,2-d]pyrimidin-4(3H)-one hydrochloride | B | B |
| 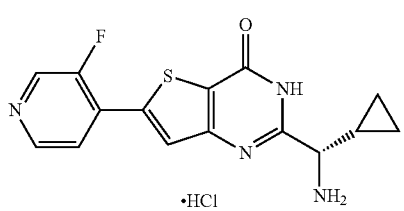 [SMILES: N[C@H](c1nc2cc(-c3ccncc3F)sc2c(=O)[nH]1)C1CC1 ; Cl] | 25 | (S)-2-(amino(cyclopropyl)methyl)-6-(3-fluoropyridin-4-yl)thieno[3,2-d]pyrimidin-4(3H)-one hydrochloride | A | A |
| 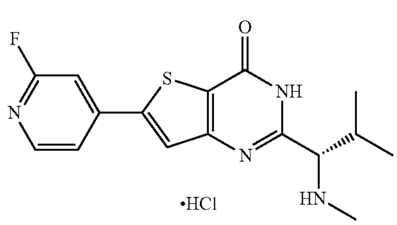 [SMILES: CN[C@H](c1nc2cc(-c3ccnc(F)c3)sc2c(=O)[nH]1)C(C)C ; Cl] | 36 | (S)-6-(2-fluoropyridin-4-yl)-2-(2-methyl-1-(methylamino)propyl)thieno[3,2-d]pyrimidin-4(3H)-one hydrochloride | C | C |
| 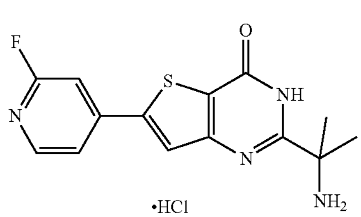 [SMILES: CC(C)(N)c1nc2cc(-c3ccnc(F)c3)sc2c(=O)[nH]1 ; Cl] | 39 | 2-(2-aminopropan-2-yl)-6-(2-fluoropyridin-4-yl)thieno[3,2-d]pyrimidin-4(3H)-one hydrochloride | C | C |

-continued

| Structure | Code | IUPAC name | CDC7 enzyme IC$_{50}$ (nm) A = < 0.1 μM B = < 1 μM C = < 10 μM D = > 10 μM | Colo 205 cell GI$_{50}$ (nm) A = < 0.1 μM B = < 1 μM C = < 10 μM D = > 10 μM |
|---|---|---|---|---|
| 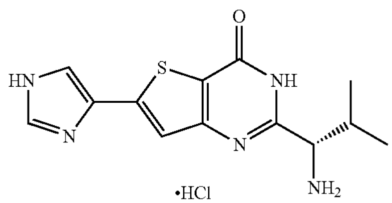 [SMILES: CC(C)[C@H](N)c1nc2cc(-c3c[nH]cn3)sc2c(=O)[nH]1 ; Cl] | 45 | (S)-2-(1-amino-2-methylpropyl)-6-(1H-imidazol-4-yl)thieno[3,2-d]pyrimidin-4(3H)-one hydrochloride | D | D |
| 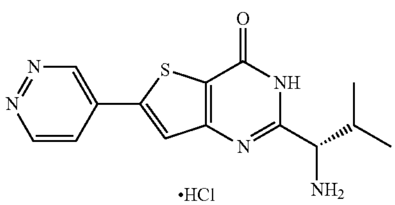 [SMILES: CC(C)[C@H](N)c1nc2cc(-c3ccnnc3)sc2c(=O)[nH]1 ; Cl] | 49 | (S)-2-(1-amino-2-methylpropyl)-6-(pyridazin-4-yl)thieno[3,2-d]pyrimidin-4(3H)-one hydrochloride | C | C |
| 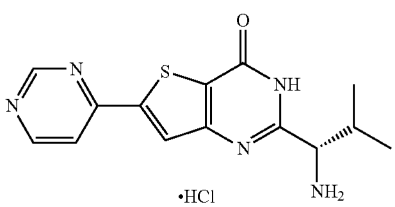 [SMILES: CC(C)[C@H](N)c1nc2cc(-c3ccncn3)sc2c(=O)[nH]1 ; Cl] | 53 | (S)-2-(1-amino-2-methylpropyl)-6-(pyrimidin-4-yl)thieno[3,2-d]pyrimidin-4(3H)-one hydrochloride | B | B |
| 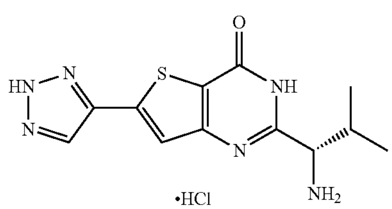 [SMILES: CC(C)[C@H](N)c1nc2cc(-c3cn[nH]n3)sc2c(=O)[nH]1 ; Cl] | 58 | (S)-2-(1-amino-2-methylpropyl)-6-(2H-1,2,3-triazol-4-yl)thieno[3,2-d]pyrimidin-4(3H)-one hydrochloride | C | C |
| 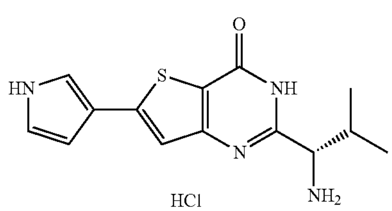 [SMILES: CC(C)[C@H](N)c1nc2cc(-c3cc[nH]c3)sc2c(=O)[nH]1 ; Cl] | 65 | (S)-2-(1-amino-2-methylpropyl)-6-(1H-pyrrol-3-yl)thieno[3,2-d]pyrimidin-4(3H)-one hydrochloride | D | D |
| | 29 | (R)-2-(1-amino-2-methylpropyl)-6-(3-fluoropyridin-4-yl)thieno[3,2-d]pyrimidin-4(3H)-one hydrochloride | C | C | a. All the compounds presented in this table and this application are chiral specific. General preparation method.

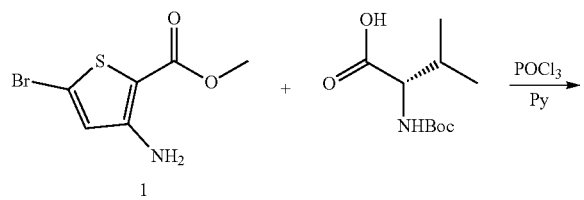

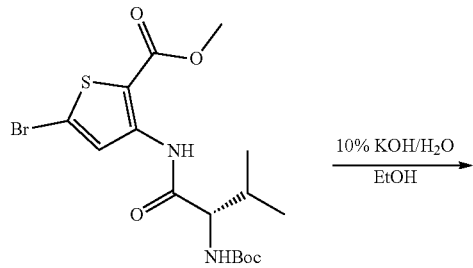

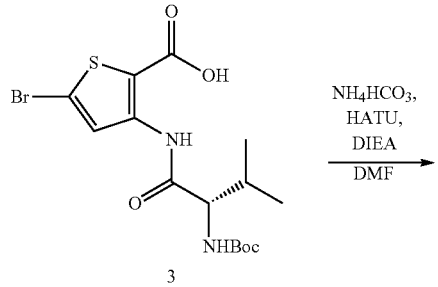

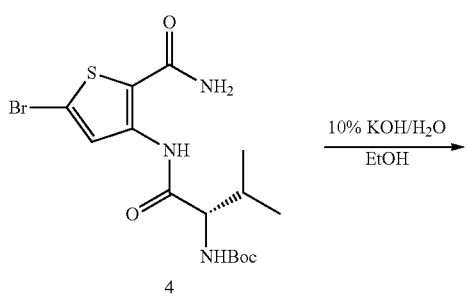

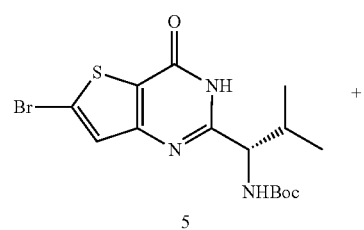

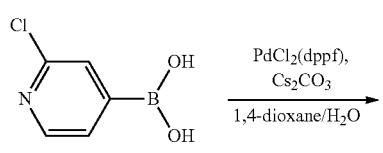

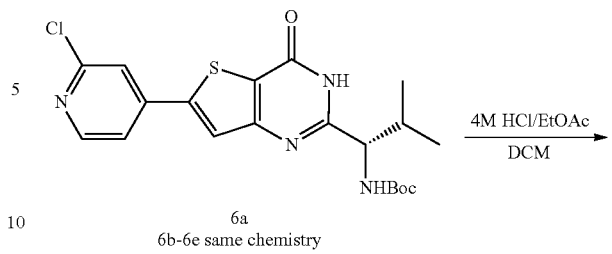

6a
6b-6e same chemistry

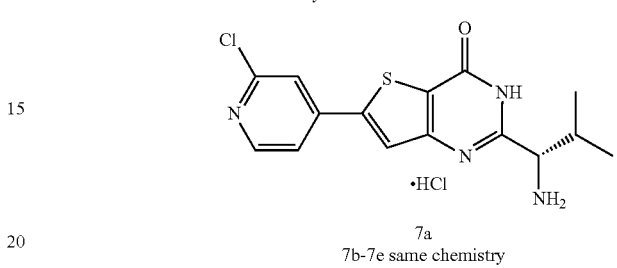

7a
7b-7e same chemistry

Example 1

1.1.1) Synthesis of (S)-methyl 5-bromo-3-(2-((tert-butoxycarbonyl)amino)-3-methylbutanamido)thiophene-2-carboxylate (Compound 2)

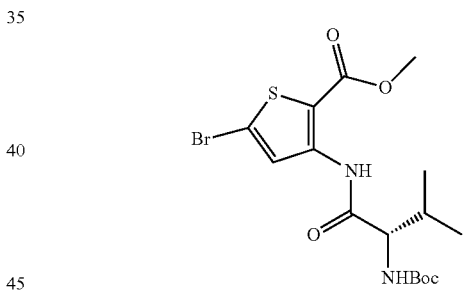

To a stirred solution of compound 1 (15.00 g, 63.54 mmol) in pyridine (250 mL) was added (S)-2-(Boc-amino)-3-methylbutyric acid (15.18 g, 69.89 mmol), the resulting dark red solution was cooled to −5° C. under $N_2$ atmosphere, Phosphorus oxychloride (11.67 g, 76.24 mmol) was added dropwise in 20 minutes, after addition, the mixture was stirred at 0° C. for 1 h, rt for 1 h, LC-MS showed that most of the start materials was consumed up, stopped the reaction, $H_2O$ (200 mL) was added, then extracted with EtOAc (250 mL*2), the combined organic layer was washed with sat. $NaHCO_3$ aq, brine, dried over anhydrous $Na_2SO_4$, concentrated in vacuo, the residue was purified by column (EtOAc/Hex 1/40 to 1/10) to give compound 2 (9.00 g, 32% yield) as a white solid. MS (ESI) (M/Z): [M+H]+=435.0, 437.0; $^1H$ NMR (400 MHz, $CDCl_3$) δ 10.64 (s, 1H), 8.22 (s, 1H), 5.09 (s, 1H), 4.17 (dd, J=18.8, 11.6 Hz, 1H), 3.89 (s, 3H), 2.34 (d, J=5.6 Hz, 1H), 1.50 (s, 9H), 1.06 (d, J=6.8 Hz, 3H), 0.97 (d, J=6.9 Hz, 3H).

1.1.2) Synthesis of (S)-5-bromo-3-(2-((tert-butoxy-carbonyl)amino)-3-methylbutanamido)thiophene-2-carboxylic acid (Compound 3)

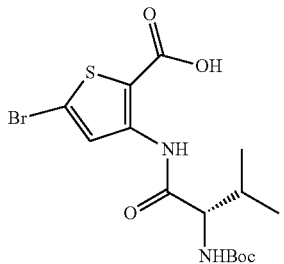 [SMILES: CC(C)[C@H](NC(=O)OC(C)(C)C)C(=O)Nc1cc(Br)sc1C(=O)O]

To a stirred solution of compound 2 (9.00 g, 20.67 mmol) in MeOH (120 mL) was added 10% KOH aq (40 mL), the mixture was heated to 70° C. for 2 h, LC-MS showed that the start materials was consumed up, stopped the reaction, cooled to rt, the pH was adjusted to 5-6 by adding 10% HCl aq, then concentrated in vacuo to remove MeOH, the residue was extracted with DCM (300 mL*2), the combined organic layer was washed with brine, dried over anhydrous $Na_2SO_4$, concentrated in vacuo to give compound 3 (8.40 g, 96% yield) as a light red solid. Used directly to the next step without further purification. MS (ESI) (M/Z): [M−H]−=419.0, 421.0

1.1.3) Synthesis of (S)-tert-butyl (1-((5-bromo-2-carbamoylthiophen-3-yl)amino)-3-methyl-1-oxobutan-2-yl)carbamate (Compound 4)

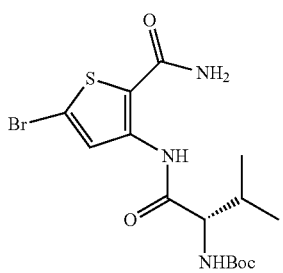 [SMILES: CC(C)[C@H](NC(=O)OC(C)(C)C)C(=O)Nc1cc(Br)sc1C(N)=O]

To a stirred solution of compound 3 (8.40 g, 19.94 mmol) in DMF (120 mL) was added HATU (9.86 g, 25.92 mmol), DIEA (7.73 g, 59.81 mmol), $NH_4HCO_3$ (4.73 g, 59.81 mmol), the mixture was stirred at rt for 15 h, LC-MS showed that the start materials was consumed up, stopped the reaction, poured into a mixture of DCM (400 mL) and $H_2O$ (500 mL), the organic layer was separated and washed with brine, dried over anhydrous $Na_2SO_4$, concentrated in vacuo, the residue was purified by column (EtOAc/Hex 1/15 to 1/3) to give compound 4 (7.20 g, 86% yield) as an off white solid. MS (ESI) (M/Z): [M+H]+=420.0, 422.0; $^1$H NMR (400 MHz, $CDCl_3$) δ 11.33 (s, 1H), 8.24 (d, J=7.8 Hz, 1H), 5.91 (s, 2H), 5.36-5.17 (m, 1H), 4.19 (dd, J=35.2, 6.9 Hz, 1H), 2.25 (dd, J=12.2, 6.1 Hz, 1H), 1.47 (d, J=12.2 Hz, 9H), 1.04 (d, J=6.8 Hz, 3H), 0.97 (d, J=6.7 Hz, 3H).

1.1.4) Synthesis of (S)-tert-butyl (1-(6-bromo-4-oxo-3,4-dihydrothieno[3,2-d]pyrimidin-2-yl)-2-methylpropyl)carbamate (Compound 5)

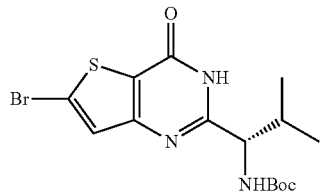 [SMILES: CC(C)[C@H](NC(=O)OC(C)(C)C)c1nc2cc(Br)sc2c(=O)[nH]1]

To a stirred solution of compound 4 (7.20 g, 17.13 mmol) in EtOH (110 mL) was added 10% KOH aq (55 mL), the mixture was heated to 70° C. for 2 h, LC-MS showed that the start materials was consumed up, stopped the reaction, cooled to rt, the pH was adjusted to 5-6 by adding 10% HCl aq, then concentrated in vacuo to remove EtOH, the residue was extracted with DCM (200 mL*2), the combined organic layer was washed with brine, dried over anhydrous $Na_2SO_4$, concentrated in vacuo to give compound 5 (5.80 g, 85% yield) as a white solid. MS (ESI) (M/Z): [M+H]+=402.0, 404.0; $^1$H NMR (400 MHz, $CDCl_3$) δ 11.77 (s, 1H), 7.36 (s, 1H), 5.50 (s, 1H), 4.55 (s, 1H), 2.30 (s, 1H), 1.45 (s, 9H), 1.02 (d, J=6.7 Hz, 6H).

1.1.5) Synthesis of (S)-tert-butyl (1-(6-(2-chloropyridin-4-yl)-4-oxo-3,4-dihydrothieno[3,2-d]pyrimidin-2-yl)-2-methylpropyl)carbamate (Compound 6a)

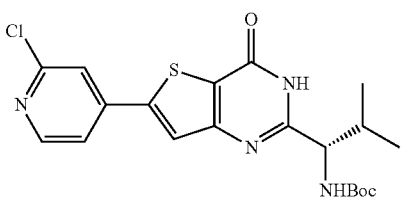 [SMILES: CC(C)[C@H](NC(=O)OC(C)(C)C)c1nc2cc(-c3ccnc(Cl)c3)sc2c(=O)[nH]1]

A suspension of compound 5 (100 mg, 0.25 mmol), 2-chloro-4-(4,4,5,5-tetramethyl-1,3,2-dioxaborolan-2-yl)pyridine (60 mg, 0.25 mmol), $PdCl_2$(dppf) (27 mg, 0.04 mmol), $Cs_2CO_3$ (162 mg, 0.50 mmol) in 1,4-dioxane (4 mL) and $H_2O$ (1 mL) was microwaved at 90° C. for 1 h, LC-MS showed that the start materials was consumed up, the reaction was repeated once at the same scale, same amount, the combined two batches were poured into a mixture of DCM (60 mL) and $H_2O$ (50 mL), the organic layer was separated and washed with brine, dried over anhydrous $Na_2SO_4$, concentrated in vacuo, the residue was purified by column (EtOAc/Hex 1/5 to 1/1) to give compound 6a (140 mg, 64% yield) as a white solid. MS (ESI) (M/Z): [M+H]+=434.2; $^1$H NMR (400 MHz, $CDCl_3$) δ 11.65 (s, 1H), 8.53 (d, J=4.9 Hz, 1H), 7.73 (s, 1H), 7.64 (s, 1H), 7.53 (d, J=4.7 Hz, 1H), 5.50 (s, 1H), 4.58 (s, 1H), 2.37 (s, 1H), 1.47 (s, 9H), 1.07 (s, 5H).

1.1.6) Synthesis of (S)-2-(1-amino-2-methylpropyl)-6-(2-chloropyridin-4-yl)thieno[3,2-d]pyrimidin-4(3H)-one hydrochloride (Compound 7a)

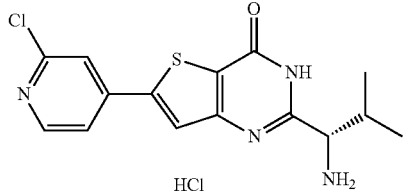 [SMILES: CC(C)[C@H](N)c1nc2cc(-c3ccnc(Cl)c3)sc2c(=O)[nH]1 ; Cl]

To a stirred suspension of compound 6a (140 mg, 0.32 mmol) in DCM (5 mL) was added 4 N HCl/EtOAc (4 mL), the mixture was heated to 40° C. for 3 h, LC-MS showed that the start materials was consumed up, stopped the reaction, cooled to rt, filtered to give compound 7a (60 mg, 56% yield) as a yellow solid. MS (ESI) (M/Z): [M+H]+=334.1; $^1$H NMR (400 MHz, DMSO) δ 13.11 (s, 1H), 8.76 (s, 3H), 8.55 (d, J=5.2 Hz, 1H), 8.14 (s, 1H), 8.09 (s, 1H), 7.92 (d, J=4.4 Hz, 1H), 4.10 (s, 1H), 2.31 (dd, J=13.7, 6.9 Hz, 1H), 1.03 (d, J=6.7 Hz, 3H), 0.96 (d, J=6.7 Hz, 3H).

1.2.1) Synthesis of (S)-tert-butyl (2-methyl-1-(6-(2-methylpyridin-4-yl)-4-oxo-3,4-dihydrothieno[3,2-d]pyrimidin-2-yl)propyl)carbamate (Compound 6b)

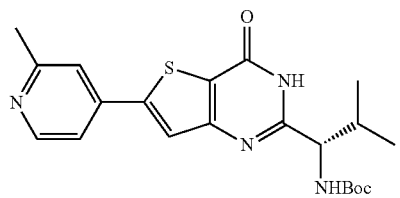 [SMILES: Cc1cc(-c2cc3nc([C@@H](NC(=O)OC(C)(C)C)C(C)C)[nH]c(=O)c3s2)ccn1]

According to 1.1.5. MS (ESI) (M/Z): [M+H]+=414.2; $^1$H NMR (400 MHz, DMSO) δ 12.50 (s, 1H), 8.56 (d, J=5.2 Hz, 1H), 8.06 (s, 1H), 7.72 (s, 1H), 7.65 (d, J=5.2 Hz, 1H), 7.09 (d, J=8.4 Hz, 1H), 4.28 (t, J=8.2 Hz, 1H), 2.56 (s, 3H), 2.13-2.01 (m, 1H), 1.43-1.21 (m, 9H), 0.95 (d, J=6.4 Hz, 3H), 0.83 (d, J=6.7 Hz, 3H).

1.2.2) Synthesis of (S)-2-(1-amino-2-methylpropyl)-6-(2-methylpyridin-4-yl)thieno[3,2-d]pyrimidin-4(3H)-one hydrochloride (Compound 7b)

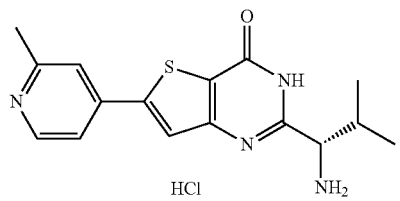 [SMILES: Cc1cc(-c2cc3nc([C@@H](N)C(C)C)[nH]c(=O)c3s2)ccn1 ; Cl]

According to 1.1.6. MS (ESI) (M/Z): [M+H]+=314.2; $^1$H NMR (400 MHz, DMSO) δ 13.25 (s, 1H), 8.84 (d, J=6.3 Hz, 4H), 8.45 (s, 1H), 8.35 (d, J=7.0 Hz, 2H), 4.14 (s, 1H), 2.81 (s, 3H), 2.32 (dt, J=13.6, 6.8 Hz, 1H), 1.05 (t, J=6.9 Hz, 3H), 0.96 (d, J=6.8 Hz, 3H).

1.3.1) Synthesis of (S)-tert-butyl (2-methyl-1-(4-oxo-6-(1H-pyrazol-3-yl)-3,4-dihydrothieno[3,2-d]pyrimidin-2-yl)propyl)carbamate (Compound 6c)

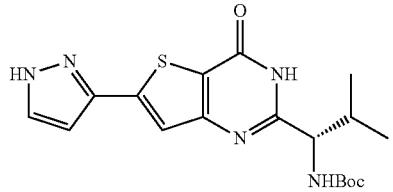 [SMILES: CC(C)[C@H](NC(=O)OC(C)(C)C)c1nc2cc(-c3cc[nH]n3)sc2c(=O)[nH]1]

According to 1.1.5. MS (ESI) (M/Z): [M+H]+=390.1; $^1$H NMR (400 MHz, DMSO) δ 13.18 (s, 1H), 12.32 (s, 1H), 7.89 (s, 1H), 7.66 (s, 1H), 7.04 (d, J=8.6 Hz, 1H), 6.88 (s, 1H), 4.27 (t, J=8.2 Hz, 1H), 2.15-2.01 (m, 1H), 1.46-1.22 (m, 9H), 0.94 (d, J=6.4 Hz, 3H), 0.83 (d, J=6.7 Hz, 3H).

1.3.2) Synthesis of (S)-2-(1-amino-2-methylpropyl)-6-(1H-pyrazol-3-yl)thieno[3,2-d]pyrimidin-4(3H)-one hydrochloride (Compound 7c)

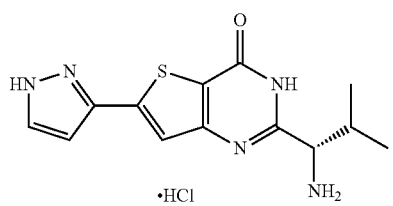 [SMILES: CC(C)[C@H](N)c1nc2cc(-c3cc[nH]n3)sc2c(=O)[nH]1 ; Cl]

According to 1.1.6. MS (ESI) (M/Z): [M+H]+=290.1; $^1$H NMR (400 MHz, DMSO) δ 12.90 (s, 1H), 8.68 (s, 3H), 7.90 (d, J=2.3 Hz, 1H), 7.65 (s, 1H), 6.96 (d, J=2.3 Hz, 1H), 4.11-4.02 (m, 1H), 2.30 (dd, J=13.8, 6.9 Hz, 1H), 1.02 (d, J=6.8 Hz, 3H), 0.96 (d, J=6.8 Hz, 3H).

1.4.1) Synthesis of (S)-tert-butyl (1-(6-(2,5-difluoropyridin-4-yl)-4-oxo-3,4-dihydrothieno[3,2-d]pyrimidin-2-yl)-2-methylpropyl)carbamate (Compound 6d)

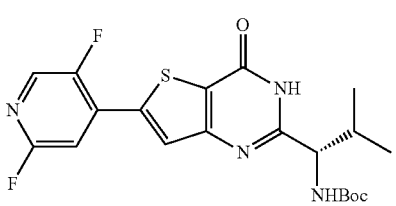 [SMILES: CC(C)[C@H](NC(=O)OC(C)(C)C)c1nc2cc(-c3cc(F)ncc3F)sc2c(=O)[nH]1]

According to 1.1.5. MS (ESI) (M/Z): [M+H]+=437.1; $^1$H NMR (400 MHz, CDCl$_3$) δ 11.46 (s, 1H), 8.25 (s, 1H), 7.90 (s, 1H), 7.27 (dd, J=4.6, 2.4 Hz, 1H), 5.46 (s, 1H), 4.55 (s, 1H), 2.38 (s, 1H), 1.47 (s, 9H), 1.06 (d, J=6.7 Hz, 6H).

1.4.2) Synthesis of (S)-2-(1-amino-2-methylpropyl)-6-(2,5-difluoropyridin-4-yl)thieno[3,2-d]pyrimidin-4(3H)-one hydrochloride (Compound 7d)

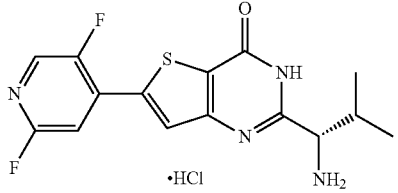 [SMILES: CC(C)[C@H](N)c1nc2cc(-c3cc(F)ncc3F)sc2c(=O)[nH]1 ; Cl]

According to 1.1.6. MS (ESI) (M/Z): [M+H]+=337.1; ¹H NMR (400 MHz, DMSO) δ 13.10 (s, 1H), 8.70 (s, 3H), 8.51 (s, 1H), 8.13 (s, 1H), 8.01 (d, J=3.2 Hz, 1H), 4.09 (d, J=7.0 Hz, 1H), 2.31 (dd, J=13.8, 6.9 Hz, 1H), 1.02 (d, J=6.8 Hz, 3H), 0.97 (d, J=6.8 Hz, 3H).

1.5.1) Synthesis of (S)-tert-butyl (1-(6-(isoxazol-4-yl)-4-oxo-3,4-dihydrothieno[3,2-d]pyrimidin-2-yl)-2-methylpropyl)carbamate (Compound 6e)

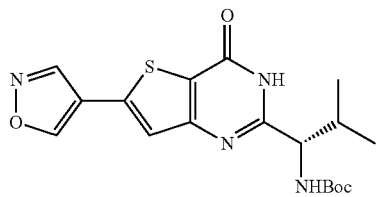 [SMILES: CC(C)[C@H](NC(=O)OC(C)(C)C)c1nc2cc(-c3cnoc3)sc2c(=O)[nH]1]

According to 1.1.5. MS (ESI) (M/Z): [M+H]+=391.1; 1H NMR (400 MHz, DMSO) δ 11.63 (s, 1H), 8.77 (s, 1H), 6.95 (d, J=8.8 Hz, 1H), 6.54 (s, 1H), 4.20 (t, J=8.5 Hz, 1H), 2.00 (s, 1H), 1.38 (s, 9H), 0.90 (d, J=6.5 Hz, 3H), 0.80 (d, J=6.7 Hz, 3H).

1.5.2) Synthesis of (S)-2-(1-amino-2-methylpropyl)-6-(isoxazol-4-yl)thieno[3,2-d]pyrimidin-4(3H)-one hydrochloride (Compound 7e)

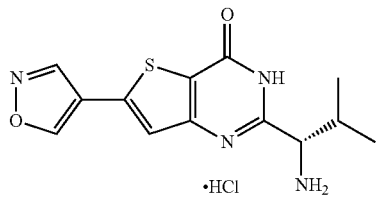 [SMILES: CC(C)[C@H](N)c1nc2cc(-c3cnoc3)sc2c(=O)[nH]1 ; Cl]

According to 1.1.6. MS (ESI) (M/Z): [M+H]+=291.1; ¹H NMR (400 MHz, DMSO) δ 12.87 (s, 1H), 8.68 (s, 4H), 8.02 (s, 1H), 7.18 (s, 1H), 4.07 (s, 1H), 2.29 (dd, J=13.6, 6.8 Hz, 1H), 1.00 (d, J=6.8 Hz, 3H), 0.94 (d, J=6.8 Hz, 3H).

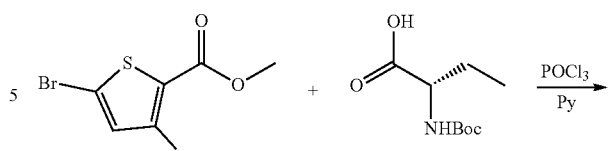

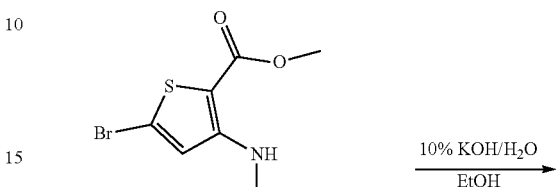

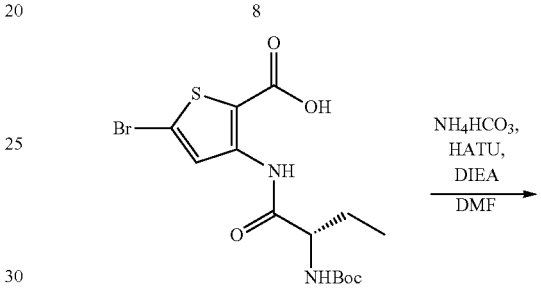

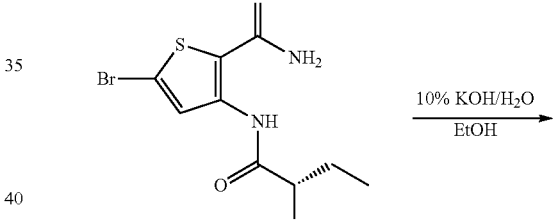

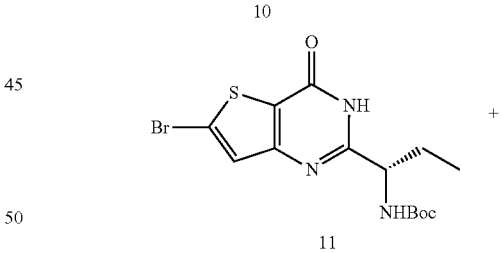

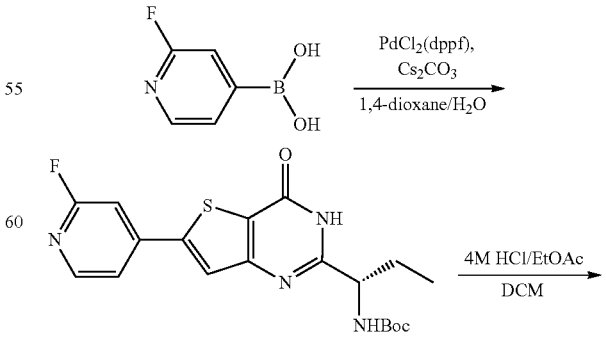

-continued

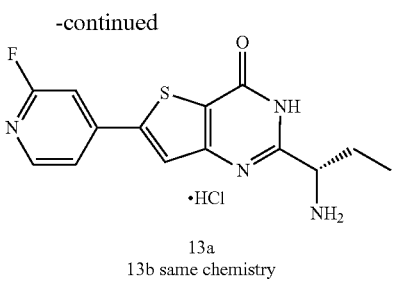

13a
13b same chemistry

Example 2

2.1.1) Synthesis of (S)-methyl 5-bromo-3-(2-((tert-butoxycarbonyl)amino)butanamido)thiophene-2-carboxylate (Compound 8)

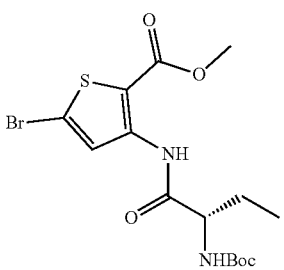 [SMILES: CC[C@H](NC(=O)OC(C)(C)C)C(=O)Nc1cc(Br)sc1C(=O)OC]

To a stirred solution of compound 1 (4.00 g, 16.94 mmol) in pyridine (60 mL) was added (S)-2-[(tert-butoxycarbonyl)amino]butanoic acid (3.79 g, 18.64 mmol), cooled to −5° C. under N$_2$ atmosphere, Phosphorus oxychloride (3.11 g, 20.33 mmol) was added dropwise in 10 minutes, after addition, the mixture was stirred at 0° C. for 1 h, rt for 1 h, LC-MS showed that most of the start materials was consumed up, stopped the reaction, H$_2$O (80 mL) was added, then extracted with EtOAc (200 mL*2), the combined organic layer was washed with sat. NaHCO$_3$ aq, brine, dried over anhydrous Na$_2$SO$_4$, concentrated in vacuo, the residue was purified by column (EtOAc/Hex 1/40 to 1/10) to give compound 8 (4.50 g, 63% yield) as a white solid. MS (ESI) (M/Z): [M+H]+=421.0, 423.0; $^1$H NMR (400 MHz, DMSO) δ 10.63 (s, 1H), 8.12 (s, 1H), 7.63 (d, J=6.4 Hz, 1H), 3.93 (s, 1H), 3.85 (s, 3H), 1.82 (dd, J=12.9, 5.9 Hz, 1H), 1.63 (ddd, J=13.9, 9.1, 7.3 Hz, 1H), 1.43 (s, 9H), 0.93 (t, J=7.3 Hz, 3H).

2.1.2) Synthesis of (S)-5-bromo-3-(2-((tert-butoxycarbonyl)amino)butanamido)thiophene-2-carboxylic acid (Compound 9)

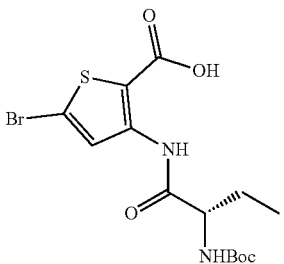 [SMILES: CC[C@H](NC(=O)OC(C)(C)C)C(=O)Nc1cc(Br)sc1C(=O)O]

To a stirred solution of compound 8 (5.20 g, 12.34 mmol) in MeOH (80 mL) was added 10% KOH aq (28 mL), the mixture was heated to 70° C. for 2 h, LC-MS showed that the start materials was consumed up, stopped the reaction, cooled to rt, the pH was adjusted to 5-6 by adding 10% HCl aq, then concentrated in vacuo to remove MeOH, the residue was extracted with DCM (200 mL*2), the combined organic layer was washed with brine, dried over anhydrous Na$_2$SO$_4$, concentrated in vacuo to give compound 9 (5.05 g, 100% yield) as a yellow solid. Used directly to the next step without further purification. MS (ESI) (M/Z): [M−H]−=405.0, 407.0

2.1.3) Synthesis of (S)-tert-butyl (1-((5-bromo-2-carbamoylthiophen-3-yl)amino)-1-oxobutan-2-yl)carbamate (Compound 10)

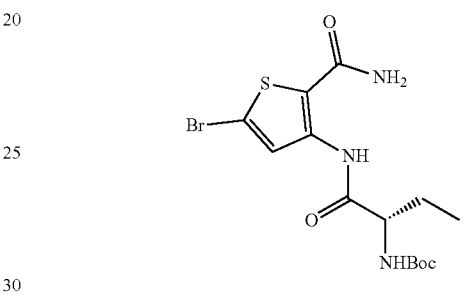

To a stirred solution of compound 9 (5.05 g, 12.40 mmol) in DMF (80 mL) was added HATU (6.13 g, 16.12 mmol), DIEA (4.81 g, 37.20 mmol), NH$_4$HCO$_3$ (2.94 g, 37.20 mmol), the mixture was stirred at rt for 15 h, LC-MS showed that the start materials was consumed up, stopped the reaction, poured into a mixture of DCM (300 mL) and H$_2$O (300 mL), the organic layer was separated and washed with brine, dried over anhydrous Na$_2$SO$_4$, concentrated in vacuo, the residue was purified by column (EtOAc/Hex 1/10 to 1/2) to give compound 10 (2.20 g, 43% yield) as an white foam. MS (ESI) (M/Z): [M+H]+=406.0, 408.0; $^1$H NMR (400 MHz, DMSO) δ 11.62 (s, 1H), 8.10 (s, 1H), 7.67 (s, 2H), 7.51 (d, J=6.8 Hz, 1H), 3.84 (t, J=10.3 Hz, 1H), 1.80 (dd, J=13.0, 5.7 Hz, 1H), 1.66-1.57 (m, 1H), 1.40 (d, J=14.6 Hz, 9H), 0.91 (t, J=7.3 Hz, 3H).

2.1.4) Synthesis of (S)-tert-butyl (1-(6-bromo-4-oxo-3,4-dihydrothieno[3,2-d]pyrimidin-2-yl)propyl)carbamate (Compound 11)

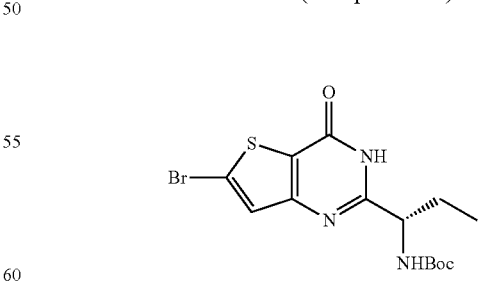

To a stirred solution of compound 10 (2.20 g, 5.41 mmol) in EtOH (35 mL) was added 10% KOH aq (17 mL), the mixture was heated to 70° C. for 2 h, LC-MS showed that the start materials was consumed up, stopped the reaction, cooled to rt, the pH was adjusted to 5-6 by adding 10% HCl aq, then concentrated in vacuo to remove EtOH, the residue was extracted with DCM (150 mL*2), the combined organic layer was washed with brine, dried over anhydrous Na₂SO₄, concentrated in vacuo to give compound 11 (1.60 g, 76% yield) as a white solid. MS (ESI) (M/Z): [M+H]+=388.0, 390.0; 1H NMR (400 MHz, DMSO) δ 12.58 (s, 1H), 7.60 (s, 1H), 7.19 (d, J=7.6 Hz, 1H), 4.41-4.26 (m, 1H), 1.81-1.65 (m, 2H), 1.37 (s, 9H), 0.88 (t, J=7.3 Hz, 3H).

2.1.5) Synthesis of (S)-tert-butyl (1-(6-(2-fluoropyridin-4-yl)-4-oxo-3,4-dihydrothieno[3,2-d]pyrimidin-2-yl)propyl)carbamate (Compound 12a)

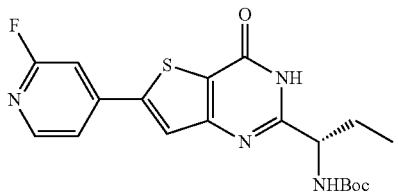 [SMILES: CC[C@H](NC(=O)OC(C)(C)C)c1nc2cc(-c3ccnc(F)c3)sc2c(=O)[nH]1]

A suspension of compound 11 (125 mg, 0.32 mmol), (2-fluoropyridin-4-yl)boronic acid (91 mg, 0.64 mmol), PdCl₂(dppf) (24 mg, 0.03 mmol), Cs₂CO₃ (315 mg, 0.97 mmol) in 1,4-dioxane (4 mL) and H₂O (1 mL) was microwaved at 90° C. for 1 h, LC-MS showed that the start materials was consumed up, stopped the reaction, cooled to rt, poured into a mixture of DCM (50 mL) and H₂O (30 mL), the organic layer was separated and washed with brine, dried over anhydrous Na₂SO₄, concentrated in vacuo, the residue was purified by column (EtOAc/Hex 1/10 to 1/2) to give compound 12a (54 mg, 41% yield) as a white solid. MS (ESI) (M/Z): [M+H]+=404.2

2.1.6) Synthesis of (S)-2-(1-aminopropyl)-6-(2-fluoropyridin-4-yl)thieno[3,2-d]pyrimidin-4(3H)-one hydrochloride (Compound 13a)

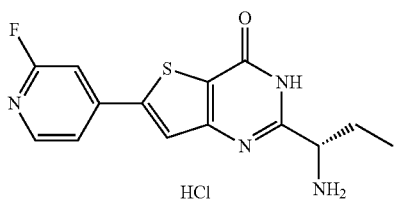 [SMILES: CC[C@H](N)c1nc2cc(-c3ccnc(F)c3)sc2c(=O)[nH]1 ; Cl]

To a stirred suspension of compound 12a (54 mg, 0.13 mmol) in DCM (10 mL) was added 4 N HCl/EtOAc (5 mL), the mixture was heated to 40° C. for 2 h, LC-MS showed that the start materials was consumed up, stopped the reaction, cooled to rt, filtered to give compound 13a (30 mg, 75% yield) as a yellow solid. MS (ESI) (M/Z): [M+H]+=304.1; ¹H NMR (400 MHz, DMSO) δ 13.13 (s, 1H), 8.74 (s, 3H), 8.33 (dd, J=45.0, 5.3 Hz, 1H), 8.15 (s, 1H), 7.94-7.39 (m, 2H), 4.27 (t, J=6.4 Hz, 1H), 2.04-1.92 (m, 2H), 0.92 (dt, J=10.1, 5.2 Hz, 3H).

2.2.1) Synthesis of (S)-tert-butyl (1-(6-(3-fluoropyridin-4-yl)-4-oxo-3,4-dihydrothieno[3,2-d]pyrimidin-2-yl)propyl)carbamate (Compound 12b)

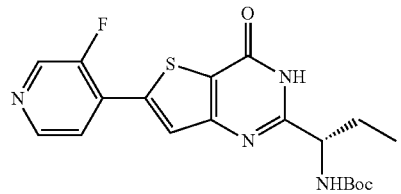 [SMILES: CC[C@H](NC(=O)OC(C)(C)C)c1nc2cc(-c3ccncc3F)sc2c(=O)[nH]1]

According to 2.1.5. MS (ESI) (M/Z): [M+H]+=405.1

2.2.2) Synthesis of (S)-2-(1-aminopropyl)-6-(3-fluoropyridin-4-yl)thieno[3,2-d]pyrimidin-4(3H)-one hydrochloride (Compound 13b)

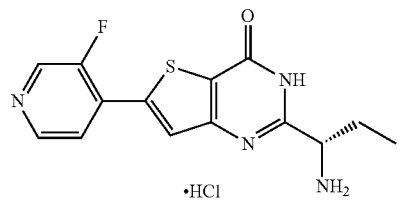

According to 2.1.6. MS (ESI) (M/Z): [M+H]+=305.1; ¹H NMR (400 MHz, DMSO) δ 13.13 (s, 1H), 8.83 (d, J=2.7 Hz, 1H), 8.77 (s, 3H), 8.60 (d, J=5.1 Hz, 1H), 8.14-8.08 (m, 1H), 8.06 (s, 1H), 4.29 (d, J=5.4 Hz, 1H), 2.08-1.94 (m, 2H), 0.93 (t, J=7.4 Hz, 3H).

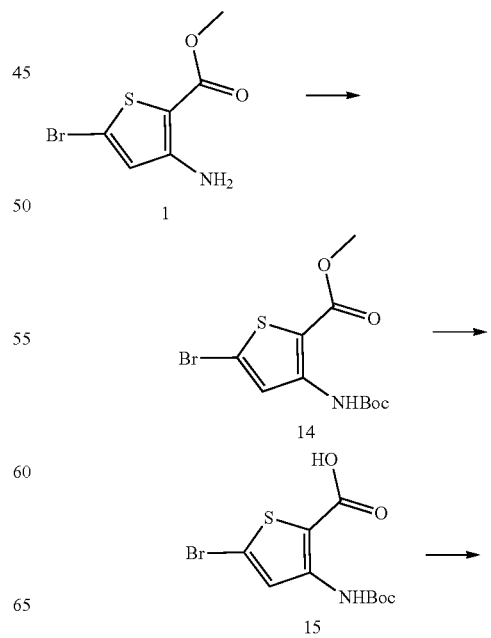

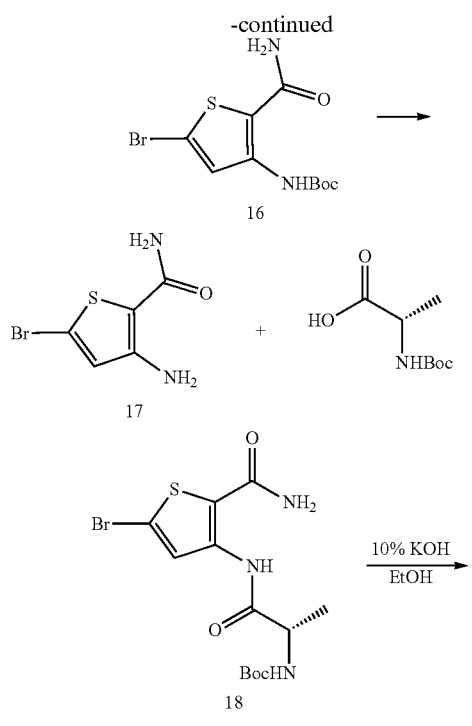

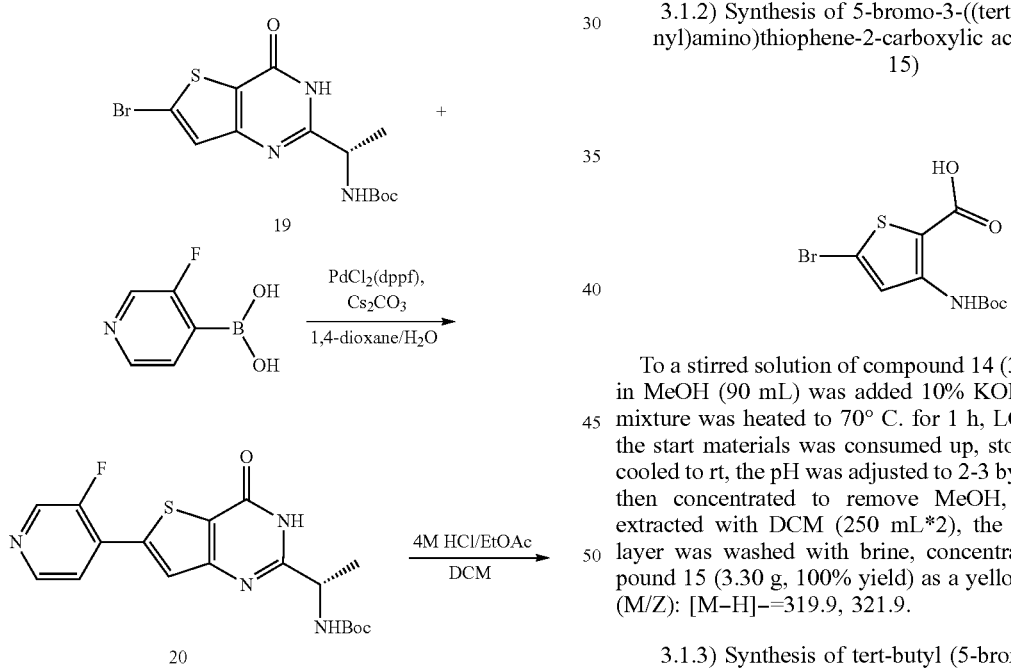

Example 3

3.1.1) Synthesis of methyl 5-bromo-3-((tert-butoxycarbonyl)amino)thiophene-2-carboxylate (Compound 14)

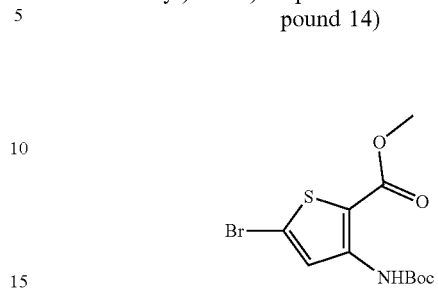

To a stirred solution of compound 1 (3.00 g, 12.71 mmol) in Py (35 mL) was added DMAP (0.16 g, 1.27 mmol) at rt, then cooled to 0° C. under N₂, Di-tert-butyl dicarbonate (3.05 g, 13.98 mmol) was added slowly in 20 minutes, after addition, the mixture was stirred at rt for 15 h, TLC showed that most of the start materials was consumed up, stopped the reaction, concentrated in vacuo, the residue was purified by column (EtOAc/Hex 1/100 to 1/30) to give compound 14 (3.30 g, 77% yield) as a white solid. MS (ESI) (M/Z): [M+H]+=336.9, 338.9; ¹H NMR (400 MHz, CDCl₃) δ 9.35 (s, 1H), 7.99 (s, 1H), 3.88 (s, 3H), 1.54 (s, 9H).

3.1.2) Synthesis of 5-bromo-3-((tert-butoxycarbonyl)amino)thiophene-2-carboxylic acid (Compound 15)

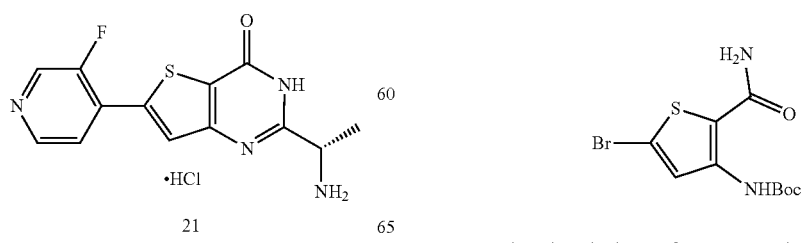

To a stirred solution of compound 14 (3.30 g, 9.82 mmol) in MeOH (90 mL) was added 10% KOH aq (30 mL), the mixture was heated to 70° C. for 1 h, LC-MS showed that the start materials was consumed up, stopped the reaction, cooled to rt, the pH was adjusted to 2-3 by adding 10% HCl, then concentrated to remove MeOH, the residue was extracted with DCM (250 mL*2), the combined organic layer was washed with brine, concentrated to give compound 15 (3.30 g, 100% yield) as a yellow solid. MS (ESI) (M/Z): [M−H]−=319.9, 321.9.

3.1.3) Synthesis of tert-butyl (5-bromo-2-carbamoylthiophen-3-yl)carbamate (Compound 16)

To a stirred solution of compound 15 (3.30 g, 10.24 mmol) in DMF (70 mL) was added HATU (5.06 g, 13.32 mmol), DIEA (3.97 g, 30.73 mmol), NH₄HCO₃ (2.43 g, 30.73 mmol), the mixture was stirred at rt for 15 h, LC-MS showed that the start materials was consumed up, stopped the reaction, poured into a mixture of DCM (200 mL) and H₂O (300 mL), the organic layer was separated and washed with brine, dried over anhydrous Na₂SO₄, concentrated in vacuo, the residue was purified by column (EtOAc/Hex 1/8 to 1/2) to give compound 16 (3.20 g, 97% yield) as a yellow solid. MS (ESI) (M/Z): [M+H]+=320.9, 322.9; ¹H NMR (400 MHz, CDCl₃) δ 10.01 (s, 1H), 8.04 (s, 1H), 5.54 (s, 2H), 1.53 (s, 9H).

3.1.4) Synthesis of 3-amino-5-bromothiophene-2-carboxamide (Compound 17)

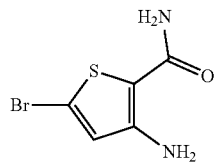

To a stirred solution of compound 16 (3.20 g, 9.96 mmol) in EtOAc (50 mL) was added 4N HCl/EtOAc (15 mL), the mixture was heated to 45° C. for 2 h, LC-MS showed that the start materials was consumed up, stopped the reaction, cooled to rt, the pH was adjusted to 7-8 by adding sat. Na₂CO₃ aq, the organic layer was separated and washed with brine, dried over anhydrous Na₂SO₄, concentrated in vacuo, the residue was purified by column (EtOAc/Hex 1/5 to 1/1) to give compound 17 (2.30 g, 100% yield) as a yellow solid. MS (ESI) (M/Z): [M+H]+=220.9, 222.9; ¹H NMR (400 MHz, CDCl₃) δ 6.60 (s, 1H), 5.74 (s, 2H), 5.42 (s, 2H).

3.1.5) Synthesis of (S)-tert-butyl (1-((5-bromo-2-carbamoylthiophen-3-yl)amino)-1-oxopropan-2-yl) carbamate (Compound 18)

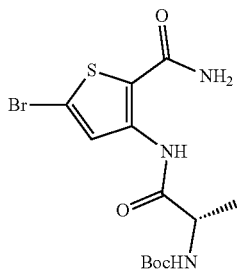 [SMILES: C[C@H](NC(=O)OC(C)(C)C)C(=O)Nc1cc(Br)sc1C(N)=O]

To a stirred solution of compound 17 (1.00 g, 4.52 mmol) in THF (100 mL) was added (S)-2-(tert-butoxycarbonylamino)propanoic acid (1.71 g, 9.05 mmol), TEA (0.92 g, 9.05 mmol), Isobutyl chloroformate (1.24 g, 9.05 mmol), the mixture was heated to reflux for 16 h, LC-MS showed that most of the start materials was consumed up, stopped the reaction, cooled to rt, EtOAc (200 mL) and H₂O (150 mL) were added, the organic layer was separated and washed with brine, dried over anhydrous Na₂SO₄, concentrated in vacuo, the residue was purified by column (EtOAc/Hex 1/5 to 1/1) to give compound 18 (850 mg, 48% yield) as a white foam. MS (ESI) (M/Z): [M+H]+=392.0, 394.0; ¹H NMR (400 MHz, CDCl₃) δ 11.37 (s, 1H), 8.23 (s, 1H), 5.77 (s, 2H), 5.20 (s, 1H), 4.35 (s, 1H), 1.49 (s, 3H), 1.48 (d, J=3.1 Hz, 9H).

3.1.6) Synthesis of (S)-tert-butyl (1-(6-bromo-4-oxo-3,4-dihydrothieno[3,2-d]pyrimidin-2-yl)ethyl) carbamate (Compound 19)

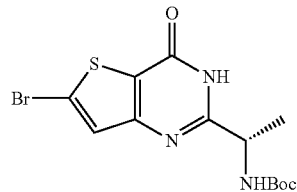 [SMILES: C[C@H](NC(=O)OC(C)(C)C)c1nc2cc(Br)sc2c(=O)[nH]1]

To a stirred solution of compound 18 (850 mg, 2.17 mmol) in EtOH (16 mL) was added 10% KOH aq (8 mL), the mixture was heated to 70° C. for 2 h, LC-MS showed that the start materials was consumed up, stopped the reaction, cooled to rt, the pH was adjusted to 5-6 by adding 10% HCl aq, then concentrated in vacuo to remove EtOH, the residue was extracted with EtOAc (100 mL*2), the combined organic layer was washed with brine, dried over anhydrous Na₂SO₄, concentrated in vacuo to give compound 19 (650 mg, 80% yield) as an off-white solid. MS (ESI) (M/Z): [M+H]+=374.0, 376.0; ¹H NMR (400 MHz, DMSO) δ 12.57 (s, 1H), 7.60 (s, 1H), 7.25 (d, J=6.9 Hz, 1H), 4.59-4.46 (m, 1H), 1.42-1.25 (m, 12H).

3.1.7) Synthesis of (S)-tert-butyl (1-(6-(3-fluoropyridin-4-yl)-4-oxo-3,4-dihydrothieno[3,2-d]pyrimidin-2-yl)ethyl)carbamate (Compound 20)

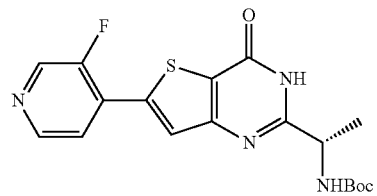 [SMILES: C[C@H](NC(=O)OC(C)(C)C)c1nc2cc(-c3ccncc3F)sc2c(=O)[nH]1]

A suspension of compound 19 (100 mg, 0.27 mmol), 3-Fluoropyridine-4-boronic acid (75 mg, 0.53 mmol), PdCl₂(dppf) (20 mg, 0.03 mmol), Cs₂CO₃ (261 mg, 0.80 mmol) in 1,4-dioxane (4 mL) and H₂O (1 mL) was microwaved at 90° C. for 1 h, LC-MS showed that the start materials was consumed up, the reaction was repeated once at the same scale, same amount, the combined two batches were poured into a mixture of DCM (60 mL) and H₂O (50 mL), the organic layer was separated and washed with brine, dried over anhydrous Na₂SO₄, concentrated in vacuo, the residue was purified by column (EtOAc/Hex 1/5 to 1/1) to give compound 20 (20 mg, 9% yield) as a light yellow solid. MS (ESI) (M/Z): [M+H]+=391.1; ¹H NMR (400 MHz, CDCl₃) δ 11.09 (s, 1H), 8.66 (d, J=2.5 Hz, 1H), 8.55 (d, J=5.0 Hz, 1H), 7.89 (s, 1H), 7.66-7.60 (m, 1H), 4.81 (s, 1H), 1.64 (s, 3H), 1.47 (d, J=11.3 Hz, 9H).

3.1.8) Synthesis of (S)-2-(1-aminoethyl)-6-(3-fluoropyridin-4-yl)thieno[3,2-d]pyrimidin-4(3H)-one hydrochloride (Compound 21)

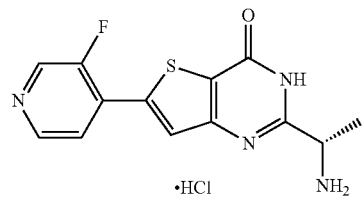 [SMILES: C[C@H](N)c1nc2cc(-c3ccncc3F)sc2c(=O)[nH]1 ; Cl]

To a stirred suspension of compound 20 (20 mg, 0.05 mmol) in EtOAc (8 mL) was added 4 N HCl/EtOAc (4 mL), the mixture was heated to 40° C. for 3 h, LC-MS showed that the start materials was consumed up, stopped the reaction, cooled to rt, filtered to give compound 21 (15 mg, 93% yield) as a yellow solid. MS (ESI) (M/Z): [M+H]+=291.0; $^1$H NMR (400 MHz, DMSO) δ 13.08 (s, 1H), 8.82 (d, J=2.4 Hz, 1H), 8.70 (s, 3H), 8.60 (d, J=4.9 Hz, 1H), 8.15-8.09 (m, 1H), 8.07 (s, 1H), 4.41 (d, J=5.6 Hz, 1H), 1.58 (d, J=6.8 Hz, 3H).

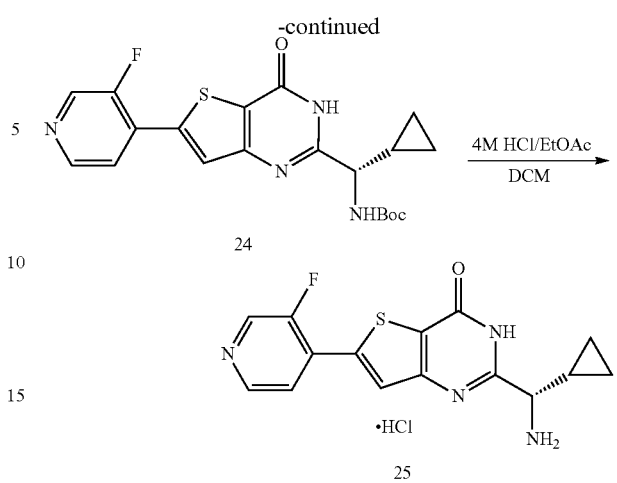

Example 4

4.1.1) Synthesis of (S)-tert-butyl (2-((5-bromo-2-carbamoylthiophen-3-yl)amino)-1-cyclopropyl-2-oxoethyl)carbamate (Compound 22)

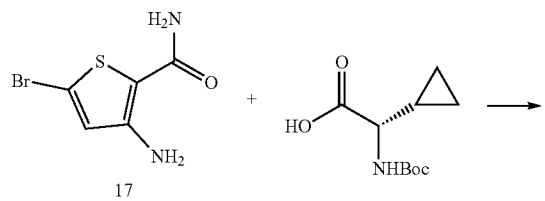

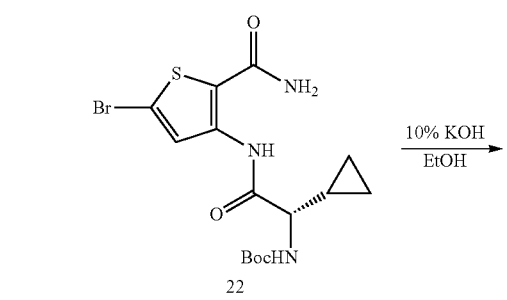

According to 3.1.5. MS (ESI) (M/Z): [M+H]+=418.0, 420.0; $^1$H NMR (400 MHz, CDCl$_3$) δ 11.33 (s, 1H), 8.26 (d, J=2.7 Hz, 1H), 5.78 (s, 2H), 5.33 (s, 1H), 3.66 (s, 1H), 1.47 (s, 9H), 1.15-1.09 (m, 1H), 0.67 (dddd, J=18.9, 14.0, 11.6, 7.3 Hz, 4H).

4.1.2) Synthesis of (S)-tert-butyl ((6-bromo-4-oxo-3,4-dihydrothieno[3,2-d]pyrimidin-2-yl)(cyclopropyl)methyl)carbamate (Compound 23)

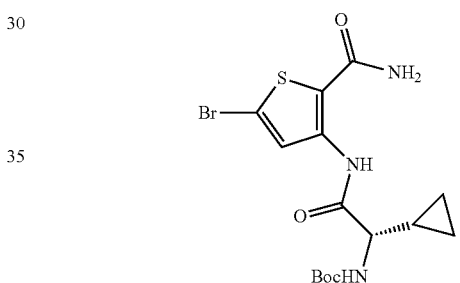

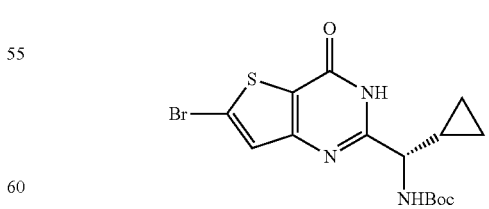

According to 3.1.6. MS (ESI) (M/Z): [M+H]+=400.0, 402.0; $^1$H NMR (400 MHz, CDCl$_3$) δ 11.97 (s, 1H), 7.37 (s, 1H), 5.66 (s, 1H), 4.03 (s, 1H), 1.43 (s, 9H), 0.90 (dd, J=13.8, 6.7 Hz, 1H), 0.67 (dd, J=8.8, 4.7 Hz, 2H), 0.60 (ddd, J=13.0, 9.6, 5.1 Hz, 2H).

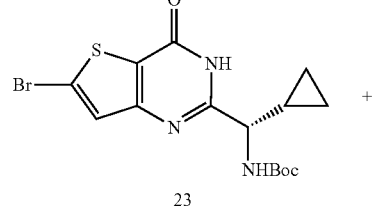

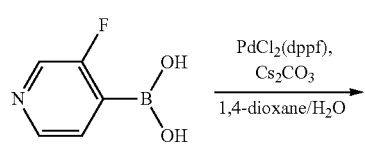

4.1.3) Synthesis of (S)-tert-butyl (cyclopropyl(6-(3-fluoropyridin-4-yl)-4-oxo-3,4-dihydrothieno[3,2-d]pyrimidin-2-yl)methyl)carbamate (Compound 24)

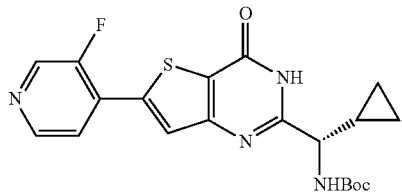 [SMILES: CC(C)(C)OC(=O)N[C@H](c1nc2cc(-c3ccncc3F)sc2c(=O)[nH]1)C1CC1]

According to 3.1.7. MS (ESI) (M/Z): [M+H]+=417.1; $^1$H NMR (400 MHz, CDCl$_3$) δ 11.17 (s, 1H), 8.66 (d, J=2.4 Hz, 1H), 8.55 (d, J=5.0 Hz, 1H), 7.91 (s, 1H), 7.68-7.60 (m, 1H), 5.54 (d, J=6.1 Hz, 1H), 3.98 (s, 1H), 1.46 (s, 9H), 0.91 (s, 1H), 0.78-0.55 (m, 4H).

4.1.4) Synthesis of (S)-2-(amino(cyclopropyl)methyl)-6-(3-fluoropyridin-4-yl)thieno[3,2-d]pyrimidin-4(3H)-one hydrochloride (Compound 25)

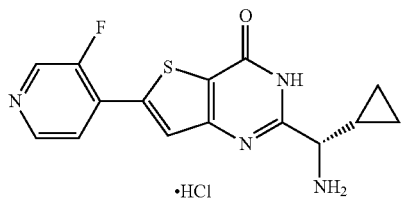

According to 3.1.8. MS (ESI) (M/Z): [M+H]+=317.1; $^1$H NMR (400 MHz, DMSO) δ 13.11 (s, 1H), 8.95 (s, 3H), 8.84 (d, J=2.6 Hz, 1H), 8.61 (d, J=5.0 Hz, 1H), 8.17-8.10 (m, 1H), 8.07 (s, 1H), 3.72 (dd, J=9.3, 5.1 Hz, 1H), 1.36-1.26 (m, 1H), 0.90-0.55 (m, 4H).

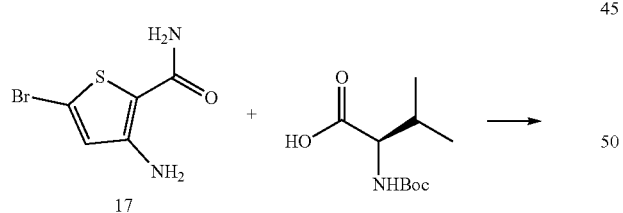

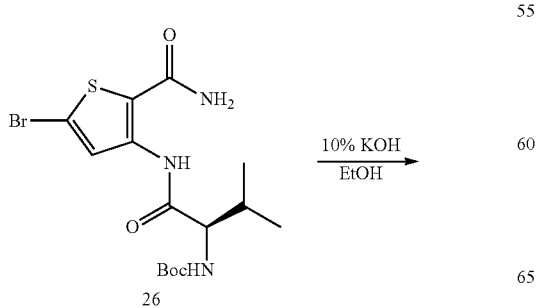

26

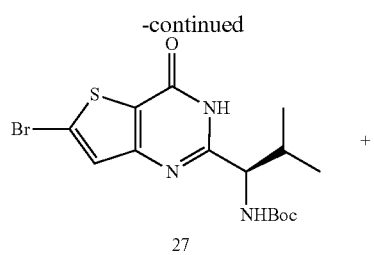

27

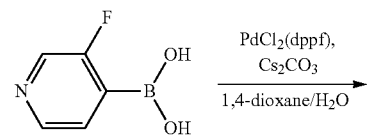

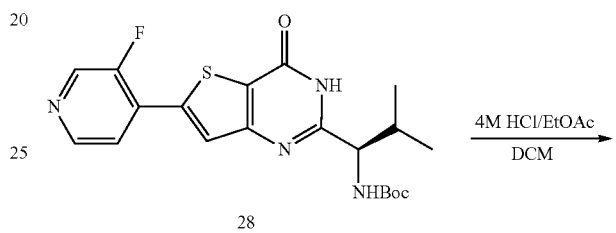

28

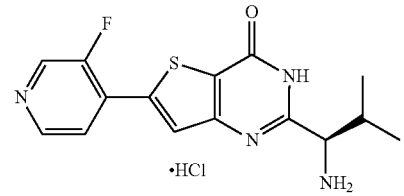

29

Example 5

5.1.1) Synthesis of (R)-tert-butyl (1-((5-bromo-2-carbamoylthiophen-3-yl)amino)-3-methyl-1-oxobutan-2-yl)carbamate (Compound 26)

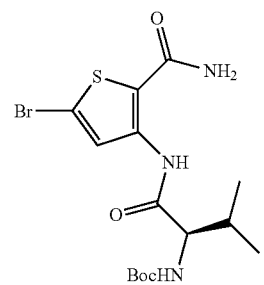 [SMILES: CC(C)[C@@H](NC(=O)OC(C)(C)C)C(=O)Nc1cc(Br)sc1C(N)=O]

According to 3.1.5. MS (ESI) (M/Z): [M+H]+=420.0, 422.0

5.1.2) Synthesis of (R)-tert-butyl (1-(6-bromo-4-oxo-3,4-dihydrothieno[3,2-d]pyrimidin-2-yl)-2-methylpropyl)carbamate (Compound 27)

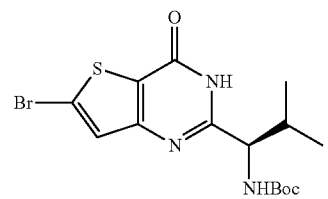 [SMILES: CC(C)[C@@H](NC(=O)OC(C)(C)C)c1nc2cc(Br)sc2c(=O)[nH]1]

According to 3.1.6. MS (ESI) (M/Z): [M+H]+=402.0, 404.0; $^1$H NMR (400 MHz, DMSO) δ 12.55 (s, 1H), 7.61 (s, 1H), 7.09 (d, J=8.5 Hz, 1H), 4.24 (t, J=8.3 Hz, 1H), 2.02 (dd, J=13.8, 7.2 Hz, 1H), 1.37 (s, 9H), 0.92 (d, J=6.5 Hz, 3H), 0.80 (d, J=6.7 Hz, 3H).

5.1.3) Synthesis of (R)-tert-butyl (1-(6-(3-fluoropyridin-4-yl)-4-oxo-3,4-dihydrothieno[3,2-d]pyrimidin-2-yl)-2-methylpropyl)carbamate (Compound 28)

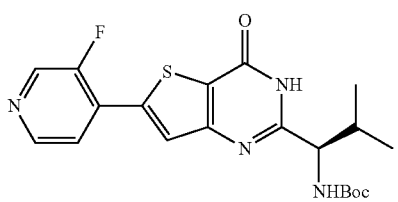 [SMILES: CC(C)[C@@H](NC(=O)OC(C)(C)C)c1nc2cc(-c3ccncc3F)sc2c(=O)[nH]1]

According to 3.1.7. MS (ESI) (M/Z): [M+H]+=419.1; $^1$H NMR (400 MHz, DMSO) δ 12.56 (s, 1H), 8.79 (d, J=2.7 Hz, 1H), 8.57 (d, J=5.1 Hz, 1H), 8.10 (s, 1H), 8.09-8.01 (m, 1H), 7.09 (d, J=8.4 Hz, 1H), 4.28 (d, J=7.9 Hz, 1H), 2.14-2.04 (m, 1H), 1.43-1.31 (m, 9H), 0.95 (d, J=6.4 Hz, 3H), 0.84 (d, J=6.7 Hz, 3H).

5.1.4) Synthesis of (R)-2-(1-amino-2-methylpropyl)-6-(3-fluoropyridin-4-yl)thieno[3,2-d]pyrimidin-4(3H)-one hydrochloride (Compound 29)

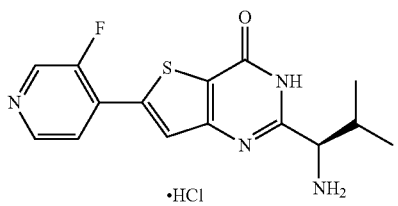 [SMILES: CC(C)[C@@H](N)c1nc2cc(-c3ccncc3F)sc2c(=O)[nH]1 ; Cl]

According to 3.1.8. MS (ESI) (M/Z): [M+H]+=319.1; $^1$H NMR (400 MHz, DMSO) δ 13.17 (s, 1H), 8.87-8.75 (m, 4H), 8.60 (d, J=5.0 Hz, 1H), 8.15-8.08 (m, 1H), 8.05 (s, 1H), 4.14 (s, 1H), 2.32 (dd, J=13.5, 6.7 Hz, 1H), 1.03 (d, J=6.7 Hz, 3H), 0.96 (d, J=6.8 Hz, 3H).

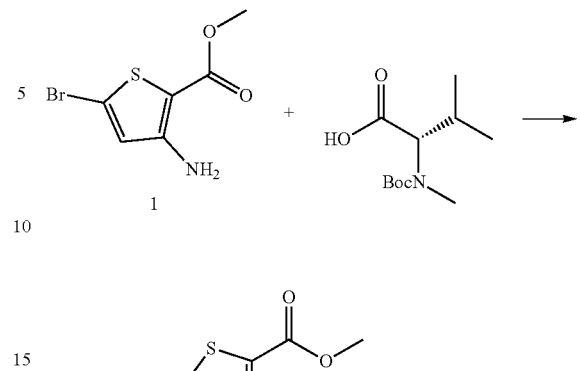
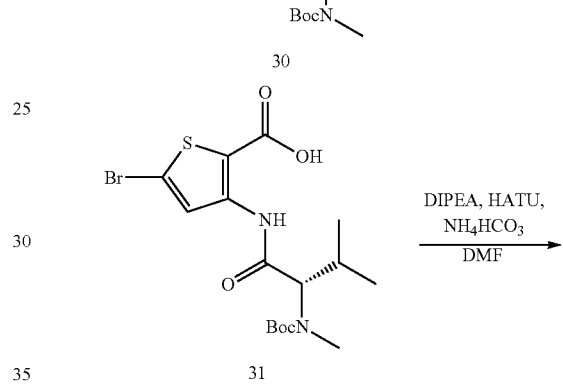
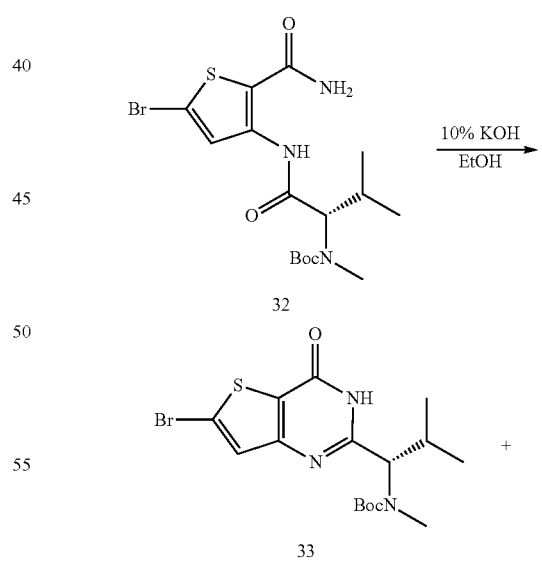
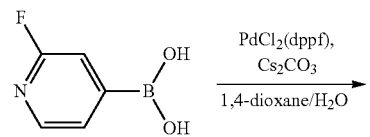

-continued

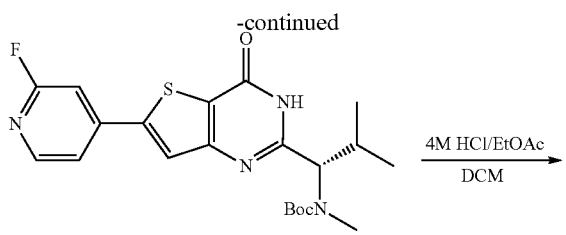

Example 6

6.1.1) Synthesis of (S)-methyl 5-bromo-3-(2-((tert-butoxycarbonyl)(methyl)amino)-3-methylbutanamido)thiophene-2-carboxylate (Compound 30)

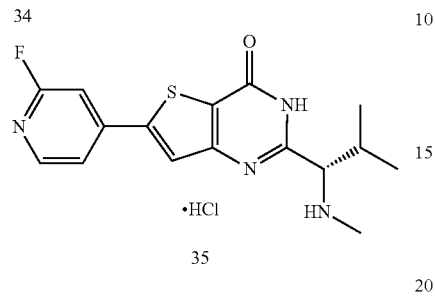

According to 3.1.5. MS (ESI) (M/Z): [M+H]+=449.0, 451.0; ¹H NMR (400 MHz, CDCl₃) δ 10.40 (s, 1H), 8.22 (s, 1H), 4.51-4.17 (m, 1H), 3.88 (d, J=7.1 Hz, 3H), 2.84 (d, J=15.9 Hz, 3H), 2.35 (s, 1H), 1.61-1.50 (m, 9H), 1.04 (d, J=5.9 Hz, 3H), 0.95 (d, J=3.9 Hz, 3H).

6.1.2) Synthesis of (S)-5-bromo-3-(2-((tert-butoxycarbonyl)(methyl)amino)-3-methylbutanamido)thiophene-2-carboxylic acid (Compound 31)

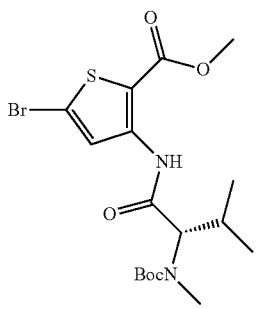 [SMILES: COC(=O)c1sc(Br)cc1NC(=O)[C@H](C(C)C)N(C)C(=O)OC(C)(C)C]

According to 1.1.2. MS (ESI) (M/Z): [M–H]–=433.0, 435.0

6.1.3) Synthesis of (S)-tert-butyl (1-((5-bromo-2-carbamoylthiophen-3-yl)amino)-3-methyl-1-oxobutan-2-yl)(methyl)carbamate (Compound 32)

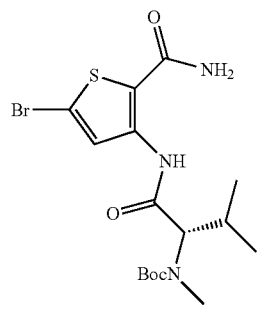 [SMILES: CC(C)[C@@H](C(=O)Nc1cc(Br)sc1C(N)=O)N(C)C(=O)OC(C)(C)C]

According to 1.1.3. MS (ESI) (M/Z): [M+H]+=434.1, 436.1; ¹H NMR (400 MHz, DMSO) δ 11.50 (d, J=24.7 Hz, 1H), 8.10 (s, 1H), 7.74 (s, 2H), 4.16 (dd, J=82.2, 8.5 Hz, 1H), 2.77 (s, 3H), 2.25 (s, 1H), 1.42 (s, 9H), 0.96 (d, J=5.1 Hz, 3H), 0.85 (d, J=6.4 Hz, 3H).

6.1.4) Synthesis of (S)-tert-butyl (1-(6-bromo-4-oxo-3,4-dihydrothieno[3,2-d]pyrimidin-2-yl)-2-methylpropyl)(methyl)carbamate (Compound 33)

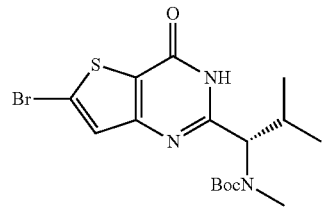 [SMILES: CC(C)[C@@H](c1nc2cc(Br)sc2c(=O)[nH]1)N(C)C(=O)OC(C)(C)C]

According to 1.1.4. MS (ESI) (M/Z): [M+H]+=416.0, 418.0; ¹H NMR (400 MHz, CDCl₃) δ 10.74 (s, 1H), 7.33 (s, 1H), 4.16 (d, J=7.1 Hz, 1H), 2.87 (s, 3H), 2.81-2.67 (m, 1H), 1.50 (s, 9H), 1.01 (d, J=6.6 Hz, 3H), 0.94 (d, J=6.4 Hz, 3H).

6.1.5) Synthesis of (S)-tert-butyl (1-(6-(2-fluoro-pyridin-4-yl)-4-oxo-3,4-dihydrothieno[3,2-d]pyrimidin-2-yl)-2-methylpropyl)(methyl)carbamate (Compound 34)

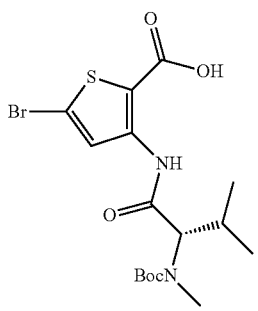

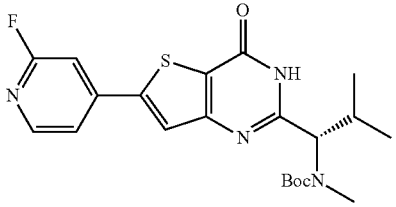 [SMILES: CC(C)[C@@H](c1nc2cc(-c3ccnc(F)c3)sc2c(=O)[nH]1)N(C)C(=O)OC(C)(C)C]

According to 1.1.5. MS (ESI) (M/Z): [M+H]+=433.1; ¹H NMR (400 MHz, CDCl₃) δ 10.76 (s, 1H), 8.34 (d, J=5.3 Hz, 1H), 7.72 (s, 1H), 7.49 (d, J=5.2 Hz, 1H), 7.29 (s, 1H), 4.17

(d, J=7.1 Hz, 1H), 2.89 (d, J=8.9 Hz, 3H), 2.80 (s, 1H), 1.52 (s, 9H), 1.05 (d, J=6.6 Hz, 3H), 0.98 (d, J=6.2 Hz, 3H).

6.1.6) Synthesis of (S)-6-(2-fluoropyridin-4-yl)-2-(2-methyl-1-(methylamino)propyl)thieno[3,2-d]pyrimidin-4(3H)-one hydrochloride (Compound 35)

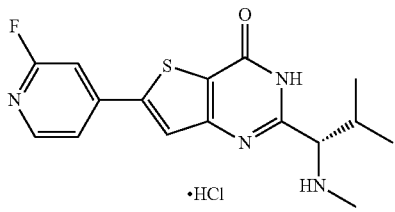 [SMILES: CN[C@H](c1nc2cc(-c3ccnc(F)c3)sc2c(=O)[nH]1)C(C)C ; Cl]

According to 1.1.6. MS (ESI) (M/Z): [M+H]+=333.1; $^1$H NMR (400 MHz, DMSO) δ 13.18 (s, 1H), 9.74 (s, 1H), 9.44 (s, 1H), 8.39 (d, J=5.3 Hz, 1H), 8.12 (s, 1H), 7.87 (d, J=5.3 Hz, 1H), 7.80 (s, 1H), 4.13 (d, J=5.5 Hz, 1H), 2.58 (s, 3H), 2.45 (dt, J=13.5, 6.8 Hz, 1H), 1.06 (d, J=6.8 Hz, 3H), 0.98 (d, J=6.8 Hz, 3H).

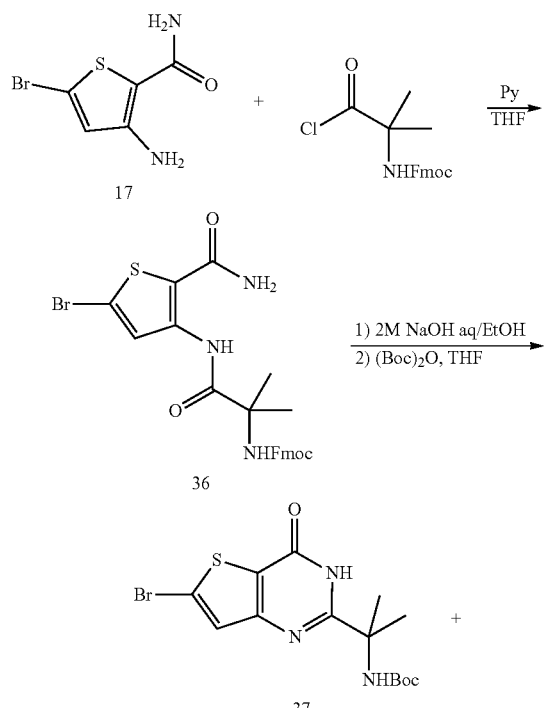

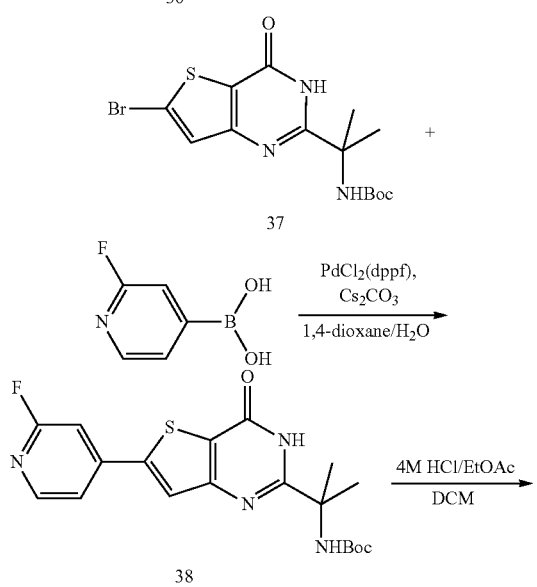

Example 7

7.1.1) Synthesis of (9H-fluoren-9-yl)methyl (1-((5-bromo-2-carbamoylthiophen-3-yl)amino)-2-methyl-1-oxopropan-2-yl)carbamate (Compound 36)

To a stirred solution of compound 17 (1.00 g, 4.52 mmol) in THF (50 mL) was added (9H-fluoren-9-yl)methyl (1-chloro-2-methyl-1-oxopropan-2-yl)carbamate (1.87 g, 5.43 mmol), Py (0.43 g, 5.43 mmol), the mixture was heated to reflux for 16 h, LC-MS showed that the start materials was consumed up, stopped the reaction, cooled to rt, added 10% HCl aq (2 mL), then concentrated in vacuo, the residue was purified by column (EtOAc/Hex 1/10 to 1/2) to give compound 36 (1.50 g, 62% yield) as a yellow solid. MS (ESI) (M/Z): [M+H]+=528.0, 530.0; $^1$H NMR (400 MHz, CDCl$_3$) δ 11.61 (s, 1H), 8.26 (s, 1H), 7.78 (d, J=6.4 Hz, 2H), 7.62 (d, J=7.6 Hz, 2H), 7.48-7.39 (m, 2H), 7.38-7.30 (m, 2H), 5.52 (s, 1H), 5.44 (s, 2H), 4.43 (s, 2H), 4.25 (s, 1H), 1.64 (s, 6H).

7.1.2) Synthesis of tert-butyl (2-(6-bromo-4-oxo-3,4-dihydrothieno[3,2-d]pyrimidin-2-yl)propan-2-yl)carbamate (Compound 37)

To a stirred solution of compound 36 (2.00 g, 3.78 mmol) in EtOH (100 mL) was added 10% KOH aq (35 mL), then heated to 80° C. for 1 h, LC-MS showed that the start materials was consumed up, stopped the reaction, the pH was adjusted to 7-8 by adding 10% HCl, then concentrated in vacuo, the residue was dissolved in THF (30 mL), added (Boc)₂O (0.99 g, 4.54 mmol), TEA (0.57 g, 5.68 mmol), stirred at rt for 16 h, LC-MS showed that the start materials was consumed up, stopped the reaction, concentrated in vacuo, the residue was purified by column (EtOAc/Hex 1/5 to 1/1) to give compound 37 (1.00 g, 68% yield) as a white solid. MS (ESI) (M/Z): [M+H]+=388.0, 390.0; ¹H NMR (400 MHz, CDCl₃) δ 11.42 (s, 1H), 7.36 (s, 1H), 5.34 (s, 1H), 1.70 (s, 6H), 1.34 (d, J=25.6 Hz, 9H).

7.1.3) Synthesis of tert-butyl (2-(6-(2-fluoropyridin-4-yl)-4-oxo-3,4-dihydrothieno[3,2-d]pyrimidin-2-yl)propan-2-yl)carbamate (Compound 38)

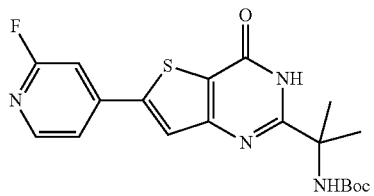 [SMILES: CC(C)(C)OC(=O)NC(C)(C)c1nc2cc(-c3ccnc(F)c3)sc2c(=O)[nH]1]

According to 1.1.5. MS (ESI) (M/Z): [M+H]+=405.1; ¹H NMR (400 MHz, DMSO) δ 12.29 (s, 1H), 8.37 (d, J=5.3 Hz, 1H), 8.25 (s, 1H), 7.83 (d, J=5.2 Hz, 1H), 7.74 (s, 1H), 7.05 (s, 1H), 1.55 (s, 6H), 1.43-1.20 (m, 9H).

7.1.4) Synthesis of 2-(2-aminopropan-2-yl)-6-(2-fluoropyridin-4-yl)thieno[3,2-d]pyrimidin-4(3H)-one hydrochloride (Compound 39)

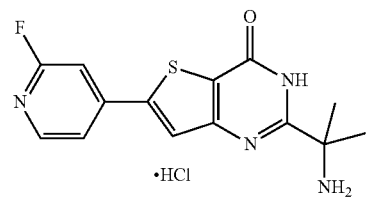 [SMILES: CC(C)(N)c1nc2cc(-c3ccnc(F)c3)sc2c(=O)[nH]1 ; Cl]

According to 1.1.6. MS (ESI) (M/Z): [M+H]+=305.1; ¹H NMR (400 MHz, DMSO) δ 12.91 (s, 1H), 8.83 (s, 3H), 8.38 (d, J=5.3 Hz, 1H), 8.21 (s, 1H), 7.88 (d, J=5.2 Hz, 1H), 7.82 (s, 1H), 1.73 (d, J=10.1 Hz, 6H).

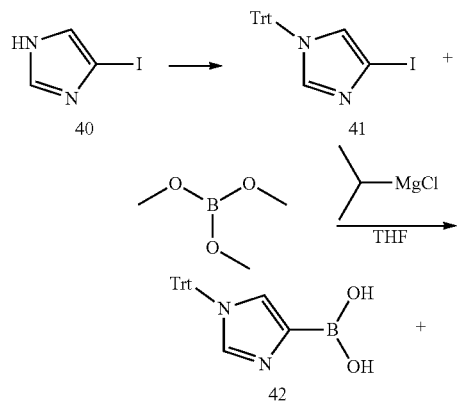

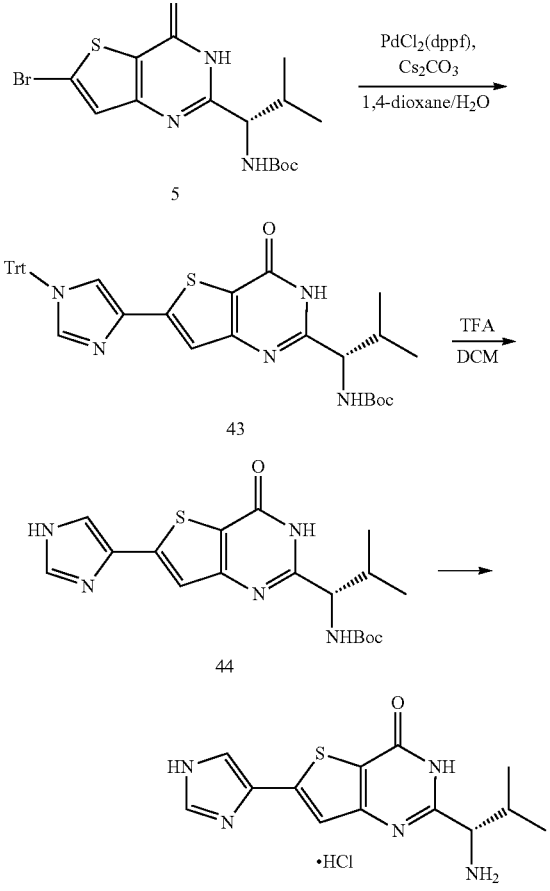

Example 8

8.1.1) Synthesis of 4-iodo-1-trityl-1H-imidazole (Compound 41)

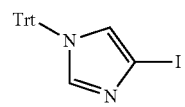

To a stirred suspension of compound 40 (5.00 g, 25.78 mmol), Triphenylmethyl chloride (8.63 g, 30.94 mmol) in DCM (100 mL) was added TEA (3.91 g, 38.67 mmol), the resulting mixture was stirred at rt for 15 h, TLC showed that the start materials was consumed up, stopped the reaction, poured into a mixture of DCM (200 mL) and H₂O (150 mL), the organic layer was separated and washed with brine, dried over anhydrous Na₂SO₄, concentrate in vacuo, the residue was purified by column (EtOAc/Hex 1/30 to 1/5) to give compound 41 (10.00 g, 88% yield) as a white solid. MS (ESI) (M/Z): [M+H]+=437.0; ¹H NMR (400 MHz, CDCl₃) δ 7.41-7.34 (m, 10H), 7.18-7.11 (m, 6H), 6.94 (d, J=1.4 Hz, 1H).

8.1.2) Synthesis of (1-trityl-1H-imidazol-4-yl)boronic acid (Compound 42)

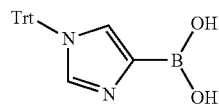

To a stirred solution of compound 41 (1.00 g, 2.29 mmol) in THF (15 mL) was added Isopropylmagnesium chloride, 2.0M solution in THF (1.72 mL, 3.44 mmol) dropwise at 0° C. in 10 minutes under $N_2$ atmosphere, after addition, the solution was stirred at 0° C. for 15 minutes, Trimethyl borate (1.19 g, 11.46 mmol) was added at 0° C. in 5 minutes, after addition, the mixture was stirred at 0° C. for 15 minutes, rt for 15 minutes, then 1 M HCl aq (10 mL) was added, stirred at rt for 10 minutes, then the mixture was poured into sat. $NaHCO_3$ aq (50 mL) slowly, extracted with EtOAc (50 ml*3), the combined organic layer was washed with brine, dried over anhydrous $Na_2SO_4$, concentrate in vacuo to give compound 42 (0.90 g, 100% yield) as a crude.

8.1.3) Synthesis of (S)-tert-butyl (2-methyl-1-(4-oxo-6-(1-trityl-1H-imidazol-4-yl)-3,4-dihydrothieno[3,2-d]pyrimidin-2-yl)propyl)carbamate (Compound 43)

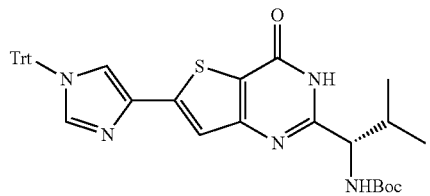

According to 1.1.5. MS (ESI) (M/Z): [M+H]+=632.2; $^1$H NMR (400 MHz, CDCl$_3$) δ 11.76 (s, 1H), 7.53 (d, J=1.0 Hz, 1H), 7.41-7.36 (m, 10H), 7.22-7.17 (m, 7H), 5.62 (d, J=8.7 Hz, 1H), 4.55 (s, 1H), 2.30 (s, 1H), 1.44 (s, 9H), 1.00 (t, J=6.1 Hz, 6H).

8.1.4) Synthesis of (S)-tert-butyl (1-(6-(1H-imidazol-4-yl)-4-oxo-3,4-dihydrothieno[3,2-d]pyrimidin-2-yl)-2-methylpropyl)carbamate (Compound 44)

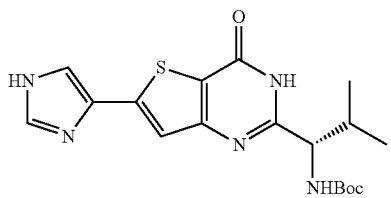 [SMILES: CC(C)[C@H](NC(=O)OC(C)(C)C)c1nc2cc(-c3c[nH]cn3)sc2c(=O)[nH]1]

To a stirred solution of compound 43 (6.00 g, 0.95 mmol) in DCM (20 mL) was added TFA (3 mL), the mixture was stirred at rt for 15 h, LC-MS showed that the start materials was consumed up, stopped the reaction, poured into a mixture of DCM (100 mL) and H$_2$O (60 mL), the pH was adjusted to 7-8 by adding NaHCO$_3$, the organic layer was separated and washed with brine, dried over anhydrous Na$_2$SO$_4$, concentrate in vacuo, the residue was purified by column (DCM/MeOH 100/1 to 10/1) to give compound 44 (40 mg, 10% yield) as a white solid. MS (ESI) (M/Z): [M+H]+=390.1; 1H NMR (400 MHz, MeOD) δ 7.82 (s, 1H), 7.71 (s, 1H), 7.52 (s, 1H), 4.35 (d, J=7.7 Hz, 1H), 2.22-2.13 (m, 1H), 1.47 (s, 9H), 1.04 (d, J=6.3 Hz, 3H), 0.97 (d, J=6.7 Hz, 3H).

8.1.5) Synthesis of (S)-2-(1-amino-2-methylpropyl)-6-(1H-imidazol-4-yl)thieno[3,2-d]pyrimidin-4(3H)-one hydrochloride (Compound 45)

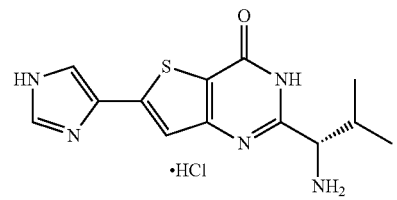 [SMILES: CC(C)[C@H](N)c1nc2cc(-c3c[nH]cn3)sc2c(=O)[nH]1 ; Cl]

According to 1.1.6. MS (ESI) (M/Z): [M+H]+=290.1; $^1$H NMR (400 MHz, DMSO) δ 13.10 (s, 1H), 9.15 (s, 1H), 8.81 (s, 3H), 8.35 (s, 1H), 8.14 (s, 1H), 7.25 (ddd, J=25.2, 15.6, 7.4 Hz, 1H), 4.12 (s, 1H), 2.30 (dd, J=13.5, 6.7 Hz, 1H), 1.01 (d, J=6.7 Hz, 3H), 0.95 (d, J=6.7 Hz, 3H).

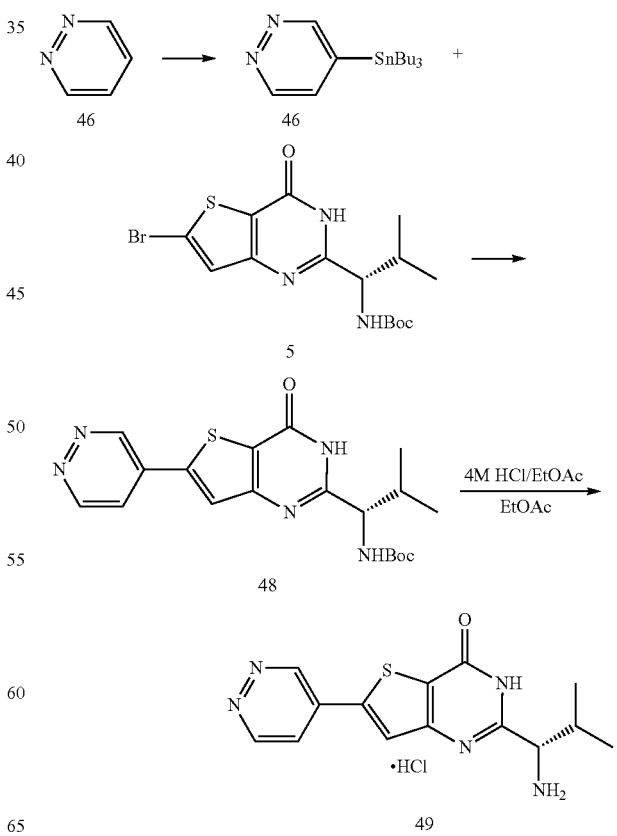

Example 9

9.1.1) Synthesis of 4-(tributylstannyl)pyridazine (Compound 47)

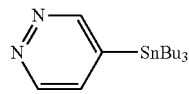

To a stirred solution of DIPEA (3.79 g, 37.46 mmol) in THF (40 mL) was added n-BuLi, 2.5M solution in Hexane (13.73 mL, 34.34 mmol) dropwise at −70° C. in 10 minutes under $N_2$ atmosphere, after addition, stirred at −70° C. for 0.5 h, warmed to −10° C. for 1 h, then the mixture was added to a solution of compound 46 (2.50 g, 31.21 mmol), SnClBu$_3$ (12.19 g, 37.46 mmol) in THF (60 mL) at −70° C. in 20 minutes under $N_2$ atmosphere, after addition, stirred at −70° C. for 1 h, then warmed to rt for 15 h, LC-MS showed that the start materials was consumed up, stopped the reaction, EtOAc (100 mL) and H$_2$O (150 mL) were added, the organic layer was separated, washed with brine, dried over anhydrous Na$_2$SO$_4$, concentrate in vacuo, the residue was purified by column (EtOAc/Hexane 1/20 to 1/5) to give compound 47 (2.20 g, 20% yield) as a brown oil. MS (ESI) (M/Z): [M+H]+=371.1; $^1$H NMR (400 MHz, CDCl$_3$) δ 9.18 (t, J=1.4 Hz, 1H), 9.04 (dd, J=4.8, 1.4 Hz, 1H), 7.55 (dd, J=4.8, 1.6 Hz, 1H), 1.63-1.46 (m, 6H), 1.35 (dd, J=14.8, 7.3 Hz, 6H), 1.16 (dd, J=21.2, 13.3 Hz, 6H), 0.94-0.89 (m, 9H).

9.1.2) Synthesis of (S)-tert-butyl (2-methyl-1-(4-oxo-6-(pyridazin-4-yl)-3,4-dihydrothieno[3,2-d]pyrimidin-2-yl)propyl)carbamate (Compound 48)

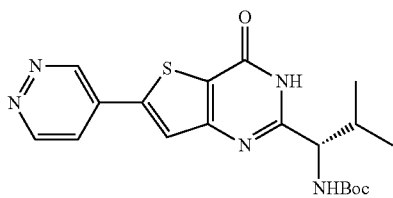 [SMILES: CC(C)[C@H](NC(=O)OC(C)(C)C)c1nc2cc(-c3ccnnc3)sc2c(=O)[nH]1]

A suspension of compound 5 (100 mg, 0.25 mmol), compound 47 (184 mg, 0.50 mmol), Pd(PPh$_3$)$_4$ (29 mg, 0.03 mmol), CuI (47 mg, 0.25 mmol) in 1,4-dioxane (4 mL) was microwaved at 100° C. for 40 minutes, LC-MS showed that the start materials was consumed up, stopped the reaction, poured into a mixture of DCM (60 mL) and H2O (50 mL), filtered through a pad of celite, the organic layer was separated, washed with brine, dried over anhydrous Na$_2$SO$_4$, concentrate in vacuo, the residue was purified by column (DCM/MeOH 100/1 to 40/1) to give compound 48 (30 mg, 30% yield) as a white solid. MS (ESI) (M/Z): [M+H]+=402.1; $^1$H NMR (400 MHz, DMSO) δ 12.58 (s, 1H), 9.79 (s, 1H), 9.36 (d, J=4.3 Hz, 1H), 8.28 (s, 1H), 8.11 (s, 1H), 7.11 (d, J=7.9 Hz, 1H), 4.29 (s, 1H), 2.09 (d, J=6.3 Hz, 1H), 1.30 (d, J=59.0 Hz, 9H), 0.95 (d, J=5.5 Hz, 3H), 0.84 (d, J=6.5 Hz, 3H).

9.1.3) Synthesis of (S)-2-(1-amino-2-methylpropyl)-6-(pyridazin-4-yl)thieno[3,2-d]pyrimidin-4(3H)-one hydrochloride (Compound 49)

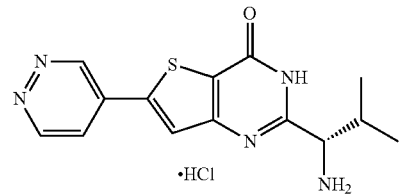 [SMILES: CC(C)[C@H](N)c1nc2cc(-c3ccnnc3)sc2c(=O)[nH]1 ; Cl]

According to 1.1.6. MS (ESI) (M/Z): [M+H]+=302.1; $^1$H NMR (400 MHz, DMSO) δ 13.17 (s, 1H), 9.87 (d, J=1.3 Hz, 1H), 9.40 (d, J=5.3 Hz, 1H), 8.81 (s, 3H), 8.24 (s, 1H), 8.22 (dd, J=5.5, 2.5 Hz, 1H), 4.12 (d, J=5.8 Hz, 1H), 2.32 (dd, J=13.6, 6.8 Hz, 1H), 1.03 (d, J=6.8 Hz, 3H), 0.96 (d, J=6.8 Hz, 3H).

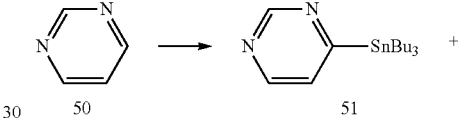

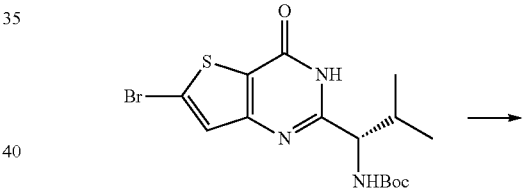

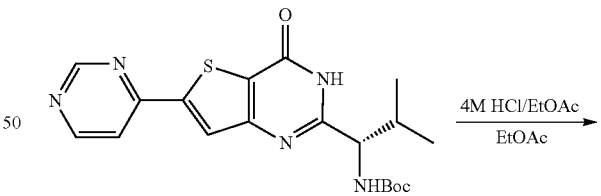

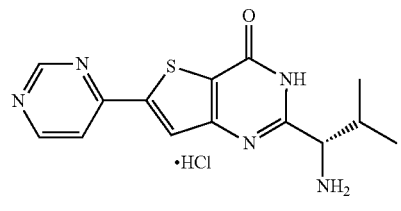

Example 10

10.1.1) Synthesis of 4-(tributylstannyl)pyrimidine (Compound 51)

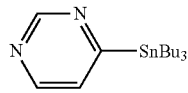

According to 9.1.1. MS (ESI) (M/Z): [M+H]+=371.1

10.1.2) Synthesis of (S)-tert-butyl (2-methyl-1-(4-oxo-6-(pyrimidin-4-yl)-3,4-dihydrothieno[3,2-d]pyrimidin-2-yl)propyl)carbamate (Compound 52)

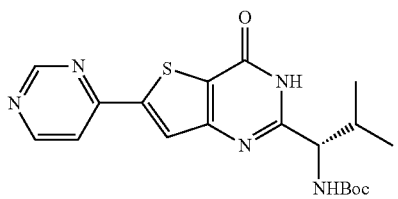 [SMILES: CC(C)[C@H](NC(=O)OC(C)(C)C)c1nc2cc(-c3ccncn3)sc2c(=O)[nH]1]

A solution of compound 5 (175 mg, 0.19 mmol), compound 51 (103 mg, 0.28 mmol), Pd(PPh$_3$)$_4$ (22 mg, 0.02 mmol) in 1,4-dioxane (4 mL) was microwaved at 100° C. for 40 minutes, LC-MS showed that the start materials was consumed up, stopped the reaction, poured into a mixture of DCM (60 mL) and H2O (50 mL), filtered through a pad of celite, the organic layer was separated, washed with brine, dried over anhydrous Na$_2$SO$_4$, concentrate in vacuo, the residue was purified by column (DCM/MeOH 100/1 to 40/1) to give compound 52 (9 mg, 11% yield) as a white solid. MS (ESI) (M/Z): [M+H]+=402.1

10.1.3) Synthesis of (S)-2-(1-amino-2-methylpropyl)-6-(pyrimidin-4-yl)thieno[3,2-d]pyrimidin-4(3H)-one hydrochloride (Compound 53)

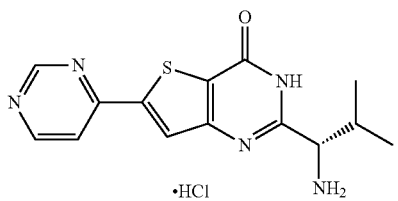

According to 1.1.6. MS (ESI) (M/Z): [M+H]+=302.1; $^1$H NMR (400 MHz, DMSO) δ 13.10 (s, 1H), 9.28 (s, 1H), 9.00 (d, J=5.3 Hz, 1H), 8.76 (s, 3H), 8.39 (d, J=4.7 Hz, 1H), 8.34 (s, 1H), 4.14-4.07 (m, 1H), 2.35-2.26 (m, 1H), 1.03 (d, J=6.8 Hz, 3H), 0.96 (d, J=6.8 Hz, 3H).

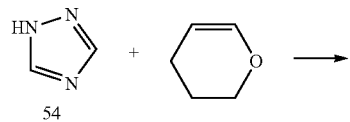

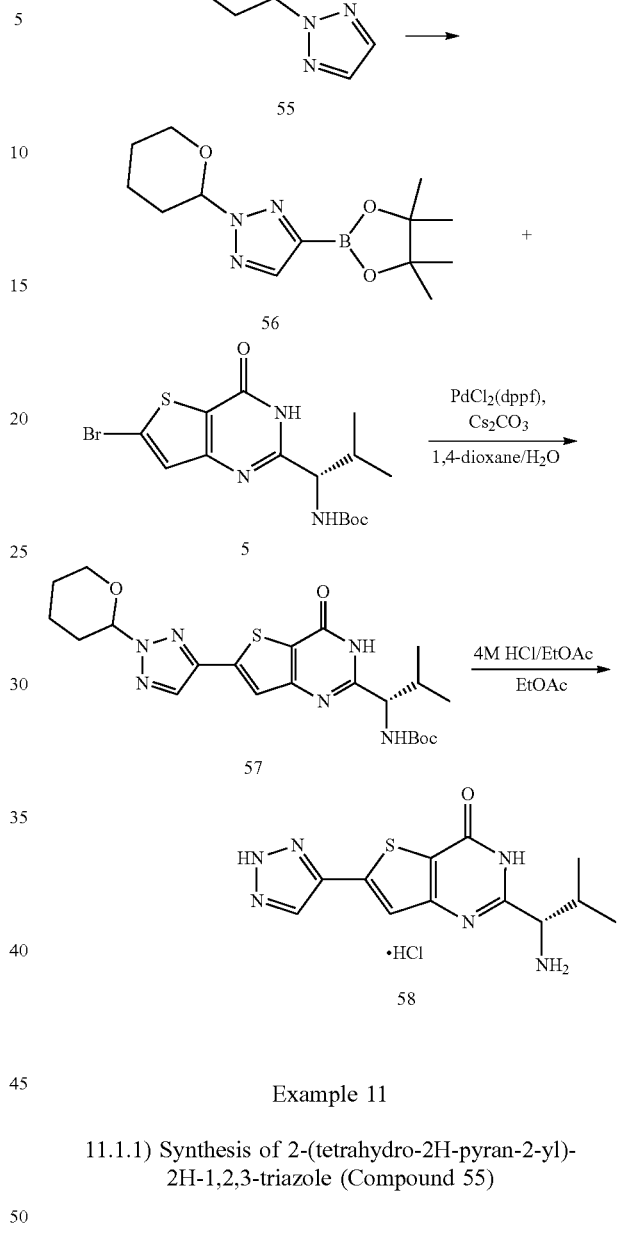

Example 11

11.1.1) Synthesis of 2-(tetrahydro-2H-pyran-2-yl)-2H-1,2,3-triazole (Compound 55)

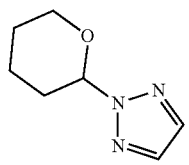 [SMILES: c1cnn(C2CCCCO2)n1]

To a stirred solution of compound 54 (5.00 g, 74.55 mmol) in DCM (100 mL) was added 3,4-dihydro-2H-pyran (6.90 g, 82.00 mmol) and p-Toluenesulfonic acid (0.62 g, 3.62 mmol), the mixture was stirred at rt for 16 h, TLC showed that the start materials was consumed up, stopped the reaction, concentrated in vacuo, the residue was purified by column (EtOAc/Hex 1/10 to 1/6) to give compound 55 (9.00 g, 81% yield) as a colorless oil. MS (ESI) (M/Z):

[M+H]+=154.1; ¹H NMR (400 MHz, CDCl₃) δ 7.67 (s, 2H), 5.73 (dd, J=9.1, 2.7 Hz, 1H), 4.03 (ddd, J=11.7, 3.7, 2.4 Hz, 1H), 3.79-3.69 (m, 1H), 2.48-2.38 (m, 1H), 2.16-2.04 (m, 2H), 1.77-1.69 (m, 2H), 1.67-1.61 (m, 1H).

11.1.2) Synthesis of 2-(tetrahydro-2H-pyran-2-yl)-4-(4,4,5,5-tetramethyl-1,3,2-dioxaborolan-2-yl)-2H-1,2,3-triazole (Compound 56)

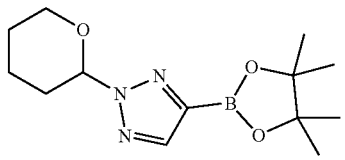 [SMILES: CC1(C)OB(c2cnn(C3CCCCO3)n2)OC1(C)C]

To a stirred suspension of DI-MU-METHOXOBIS(1,5-CYCLOOCTADIENE)DIIRIDIUM(I) (0.16 g, 0.24 mmol) in Hexane (20 mL) was added 4,4'-Di-tert-butyl-2,2'-dipyridyl (0.13 g, 0.49 mmol), the mixture was degassed with N2 for twice, then 4,4,5,5-tetramethyl-1,3,2-dioxaborolane (1.15 g, 8.98 mmol) was added, stirred at rt for 15 minutes, compound 55 (1.25 g, 8.16 mmol) was added, the mixture was stirred at rt for 16 h, TLC showed that the start materials was consumed up, stopped the reaction, concentrated in vacuo, the residue was purified by column (EtOAc/Hex 1/10 to 1/3) to give compound 56 (1.00 g, 44% yield) as a light green solid. ¹H NMR (400 MHz, CDCl₃) δ 7.97 (s, 1H), 5.80 (dd, J=9.4, 2.6 Hz, 1H), 4.10-4.02 (m, 1H), 3.76-3.67 (m, 1H), 2.53-2.40 (m, 1H), 2.17-2.01 (m, 3H), 1.72 (qd, J=11.6, 3.3 Hz, 2H), 1.63 (ddd, J=9.0, 5.4, 2.9 Hz, 1H), 1.36 (s, 12H).

11.1.3) Synthesis of tert-butyl ((1S)-2-methyl-1-(4-oxo-6-(2-(tetrahydro-2H-pyran-2-yl)-2H-1,2,3-triazol-4-yl)-3,4-dihydrothieno[3,2-d]pyrimidin-2-yl)propyl)carbamate (Compound 57)

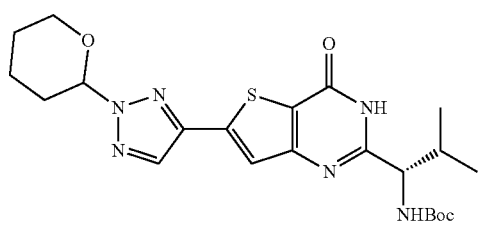 [SMILES: CC(C)[C@H](NC(=O)OC(C)(C)C)c1nc2cc(-c3cnn(C4CCCCO4)n3)sc2c(=O)[nH]1]

According to 1.1.5. MS (ESI) (M/Z): [M+H]+=475.2; ¹H NMR (400 MHz, DMSO) δ 12.47 (s, 1H), 8.50 (s, 1H), 7.89 (s, 1H), 7.08 (d, J=8.6 Hz, 1H), 5.84 (dd, J=9.1, 2.5 Hz, 1H), 4.28 (t, J=8.3 Hz, 1H), 3.92 (d, J=9.9 Hz, 1H), 3.78-3.69 (m, 1H), 2.28 (dd, J=17.3, 6.2 Hz, 1H), 2.10-1.98 (m, 3H), 1.76 (d, J=5.8 Hz, 1H), 1.65-1.54 (m, 2H), 1.44-1.24 (m, 9H), 0.94 (d, J=6.5 Hz, 3H), 0.83 (d, J=6.7 Hz, 3H).

11.1.4) Synthesis of (S)-2-(1-amino-2-methylpropyl)-6-(2H-1,2,3-triazol-4-yl)thieno[3,2-d]pyrimidin-4(3H)-one hydrochloride (Compound 58)

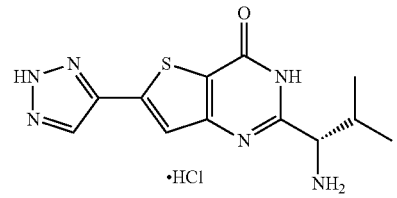 [SMILES: CC(C)[C@H](N)c1nc2cc(-c3cn[nH]n3)sc2c(=O)[nH]1 ; Cl]

To a stirred solution of compound 57 (350 mg, 0.74 mmol) in EtOAc (40 mL) was added 4 N HCl/EtOAc (15 mL), the mixture was heated to 45° C. for 2 h, LC-MS showed that the start materials was consumed up, stopped the reaction, cooled to rt, filtered to give compound 57 (220 mg, 91% yield) as a white solid. MS (ESI) (M/Z): [M+H]+=291.1; 1H NMR (400 MHz, DMSO) δ 12.99 (s, 1H), 8.73 (d, J=3.5 Hz, 3H), 8.68 (s, 1H), 7.78 (s, 1H), 4.09 (d, J=5.8 Hz, 1H), 2.30 (dd, J=13.7, 6.9 Hz, 1H), 1.02 (d, J=6.8 Hz, 3H), 0.96 (d, J=6.8 Hz, 3H).

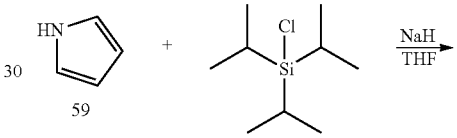

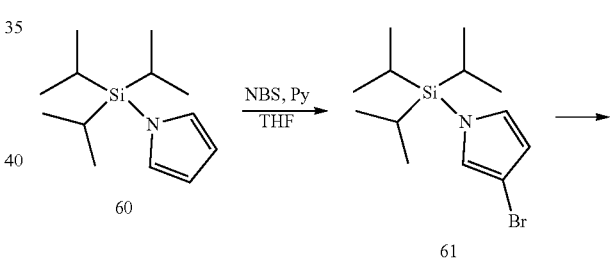

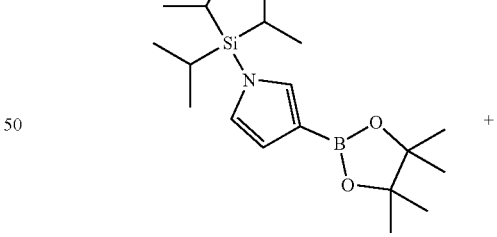

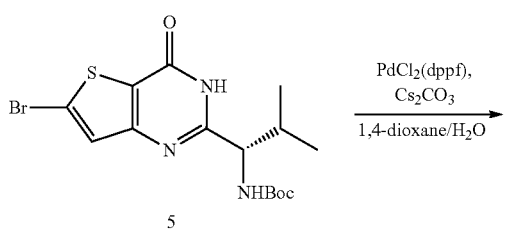

-continued

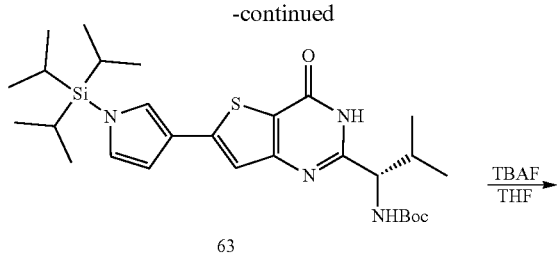

63

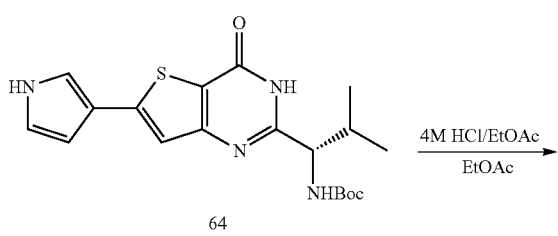

64

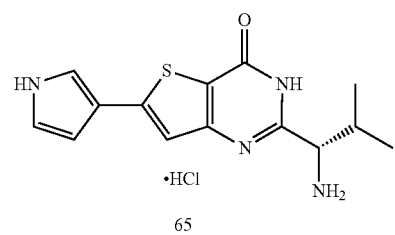

65

Example 12

12.1.1) Synthesis of 1-(triisopropylsilyl)-1H-pyrrole (Compound 60)

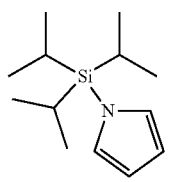

To a stirred solution of compound 59 (2.00 g, 29.81 mmol) in THF (30 mL) was added 60% NaH (1.43 g, 35.77 mmol) at 0° C. under $N_2$, then stirred at 0° C. for 1 h, a solution of chlorotriisopropylsilane (6.32 g, 32.79 mmol) in THF (20 mL) was added, stirred at 0° C. for 1 h, stopped the reaction, $H_2O$ (100 mL) was added, the mixture was extracted with EtOAc (100 mL*2), the combined organic layer was washed with brine, dried over anhydrous $Na_2SO_4$, concentrated in vacuo to give compound 60 (7.60 g, 100% yield) as a brown oil. $^1H$ NMR (400 MHz, $CDCl_3$) δ 6.90-6.79 (m, 2H), 6.41-6.31 (m, 2H), 1.49 (dt, J=15.0, 7.5 Hz, 2H), 1.14 (d, J=7.5 Hz, 9H).

12.1.2) Synthesis of 3-bromo-1-(triisopropylsilyl)-1H-pyrrole (Compound 61)

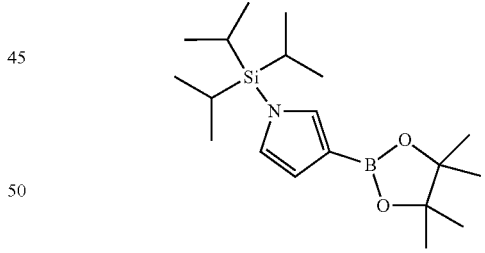

To a stirred solution of compound 60 (7.60 g, 34.02 mmol) in THF (100 mL) was added NBS (6.66 g, 37.42 mmol) at −70° C. under $N_2$, then stirred at −70° C. for 5 h, Py (1.5 mL) and n-Hexane (30 mL) were added, the mixture was warmed to rt for 1 h, concentrated in vacuo, the residue was purified by column (EtOAc/Hex 1/50 to 1/30) to give compound 61 (6.50 g, 63% yield) as a light brown oil. $^1H$ NMR (400 MHz, $CDCl_3$) δ 6.84 (dd, J=4.3, 2.4 Hz, 0H), 6.73 (dt, J=5.0, 2.2 Hz, 0H), 6.34 (dd, J=6.4, 4.5 Hz, 0H), 1.52-1.43 (m, 3H), 1.13 (dd, J=7.5, 3.6 Hz, 6H).

12.1.3) Synthesis of 3-(4,4,5,5-tetramethyl-1,3,2-dioxaborolan-2-yl)-1-(triisopropylsilyl)-1H-pyrrole (Compound 62)

To a stirred solution of compound 61 (6.50 g, 21.50 mmol), 4,4,5,5-tetramethyl-1,3,2-dioxaborolane (4.13 g, 32.25 mmol) in toluene (120 mL) was added $PdCl_2(ACN)_2$ (0.45 g, 1.72 mmol), Dicyclohexy(2',6'-dimethoxybiphenyl-2-yl)phosphine (2.65 g, 6.45 mmol), TEA (6.53 g, 64.50 mmol), the mixture was degassed with N2 for twice, then heated to 90° C. for 16 h, TLC showed that the start materials was consumed up, stopped the reaction, cooled to rt, diluted with EtOAc (200 mL), filtered through a pad of celite, the filtrate was concentrated in vacuo, the residue was purified by column (EtOAc/Hex 1/200 to 1/50) to give compound 62 (3.50 g, 46% yield) as a white solid.

12.1.4) Synthesis of (S)-tert-butyl (2-methyl-1-(4-oxo-6-(1-(triisopropylsilyl)-1H-pyrrol-3-yl)-3,4-dihydrothieno[3,2-d]pyrimidin-2-yl)propyl)carbamate (Compound 63)

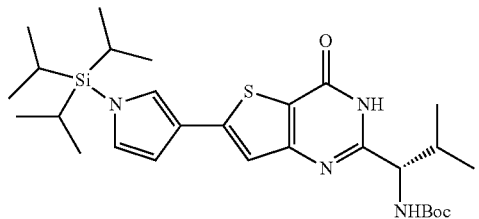 [SMILES: CC(C)[C@H](NC(=O)OC(C)(C)C)c1nc2cc(-c3ccn([Si](C(C)C)(C(C)C)C(C)C)c3)sc2c(=O)[nH]1]

According to 1.1.5. MS (ESI) (M/Z): [M+H]+=545.3; $^1$H NMR (400 MHz, CDCl$_3$) δ 11.88 (s, 1H), 7.27 (s, 1H), 7.18 (s, 1H), 6.83 (t, J=2.2 Hz, 1H), 6.63 (s, 1H), 5.71 (d, J=8.8 Hz, 1H), 4.58 (s, 1H), 2.32 (s, 1H), 1.52 (dd, J=15.0, 7.5 Hz, 3H), 1.46 (d, J=10.0 Hz, 9H), 1.16 (d, J=7.5 Hz, 18H), 1.02 (t, J=10.2 Hz, 6H).

12.1.5) Synthesis of (S)-tert-butyl (2-methyl-1-(4-oxo-6-(1H-pyrrol-3-yl)-3,4-dihydrothieno[3,2-d]pyrimidin-2-yl)propyl)carbamate (Compound 64)

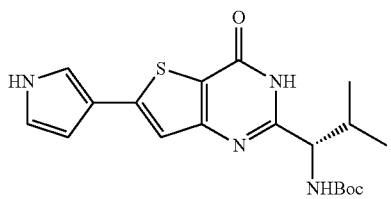

To a stirred solution of compound 63 (440 mg, 0.81 mmol) in THF (20 mL) was added TBAF (1 mol/L THF solution, 0.9 mL, 0.90 mmol) at rt, then stirred at rt for 2 h, LC-MS showed that the start materials was consumed up, stopped the reaction, concentrated in vacuo, the residue was purified by column (DCM/MeOH 100/1 to 30/1) to give compound 64 (260 Mg, 83% yield) as a white solid. MS (ESI) (M/Z): [M+H]+=389.1; $^1$H NMR (400 MHz, DMSO) δ 12.15 (s, 1H), 11.27 (s, 1H), 7.39 (s, 1H), 7.32 (s, 1H), 7.01 (d, J=8.8 Hz, 1H), 6.87 (dd, J=4.5, 2.4 Hz, 1H), 6.48 (d, J=1.7 Hz, 1H), 4.25 (t, J=8.4 Hz, 1H), 2.12-1.99 (m, 1H), 1.31 (d, J=55.1 Hz, 9H), 0.93 (d, J=6.4 Hz, 3H), 0.82 (d, J=6.7 Hz, 3H).

12.1.6) Synthesis of (S)-2-(1-amino-2-methylpropyl)-6-(1H-pyrrol-3-yl)thieno[3,2-d]pyrimidin-4(3H)-one hydrochloride (Compound 65)

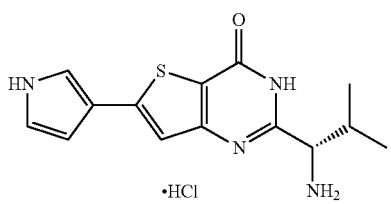

According to 1.1.6. MS (ESI) (M/Z): [M+H]+=289.1; $^1$H NMR (400 MHz, DMSO) δ 12.73 (s, 1H), 11.38 (s, 1H), 8.68 (s, 3H), 7.45 (d, J=2.5 Hz, 1H), 7.31 (s, 1H), 6.89 (dd, J=4.6, 2.5 Hz, 1H), 6.52 (dd, J=4.1, 2.3 Hz, 1H), 4.03 (s, 1H), 2.33-2.24 (m, 1H), 1.01 (d, J=6.8 Hz, 3H), 0.95 (d, J=6.8 Hz, 3H).

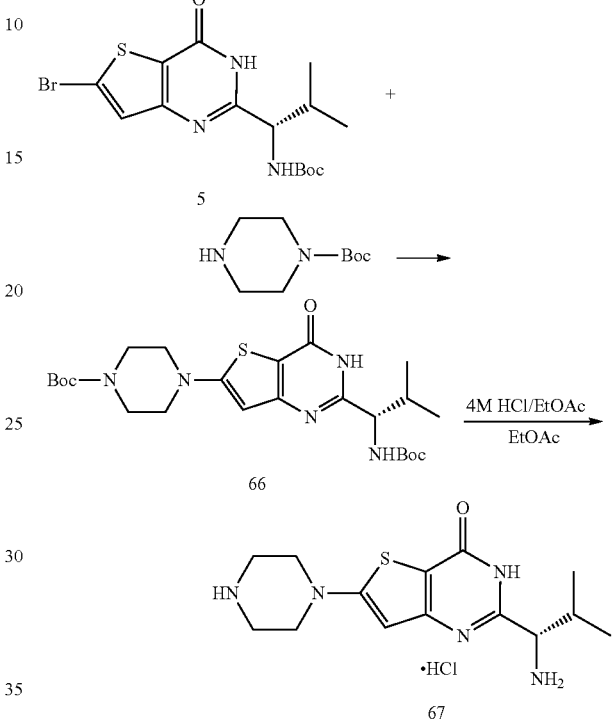

Example 13

13.1.1) Synthesis of (S)-tert-butyl 4-(2-(1-((tert-butoxycarbonyl)amino)-2-methylpropyl)-4-oxo-3,4-dihydrothieno[3,2-d]pyrimidin-6-yl)piperazine-1-carboxylate (Compound 66)

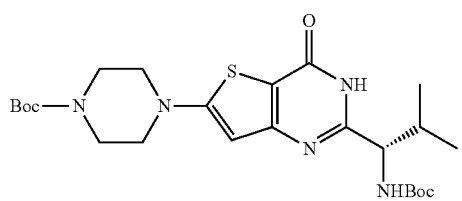 [SMILES: CC(C)[C@H](NC(=O)OC(C)(C)C)c1nc2cc(N3CCN(C(=O)OC(C)(C)C)CC3)sc2c(=O)[nH]1]

To a stirred solution of compound 5 (500 mg, 1.24 mmol) in DMSO (10 mL) was added tert-butyl piperazine-1-carboxylate (350 mg, 1.86 mmol), CuI (59 mg, 0.31 mmol), L-proline (71 mg, 0.62 mmol), the mixture was degassed with N$_2$ for twice, then heated to 100° C. for 15 h, LC-MS showed that most of the start materials was consumed up, stopped the reaction, cooled to rt, poured into a mixture of DCM (100 mL) and H$_2$O (100 mL), the organic layer was separated, washed with brine, dried over anhydrous Na$_2$SO$_4$, concentrate in vacuo, the residue was purified by column (DCM/MeOH 50/1 to 10/1) to give compound 66 (150 mg, 23% yield) as a brown solid. MS (ESI) (M/Z): [M+H]+=508.2; 1H NMR (400 MHz, CDCl₃) δ 10.88-10.64 (m, 1H), 6.22 (s, 1H), 4.44 (s, 1H), 3.64 (s, 4H), 3.34 (s, 4H), 2.34 (s, 1H), 1.51 (s, 9H), 1.46 (s, 9H), 1.00 (t, J=7.7 Hz, 6H).

13.1.2) Synthesis of (S)-2-(1-amino-2-methylpropyl)-6-(piperazin-1-yl)thieno[3,2-d]pyrimidin-4(3H)-one hydrochloride (Compound 67)

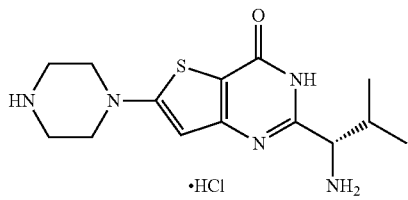 [SMILES: CC(C)[C@H](N)c1nc2cc(N3CCNCC3)sc2c(=O)[nH]1 ; Cl]

According to 1.1.6. MS (ESI) (M/Z): [M+H]+=308.1; ¹H NMR (400 MHz, MeOD) δ 6.50 (s, 1H), 4.09 (d, J=6.2 Hz, 1H), 3.69 (s, 4H), 3.45 (s, 4H), 2.36 (d, J=6.7 Hz, 1H), 1.09 (d, J=6.8 Hz, 6H).

What is claimed is:

1. A compound represented by formula (V):

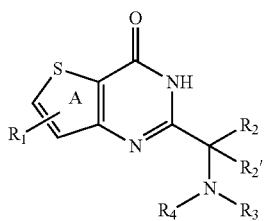

or a pharmaceutically acceptable salt thereof, wherein
$R_1$ represents pyridyl;
$R_1$ can be at any possible position on A ring;
$R_2$ represents an aliphatic substitution group with C1-20 hydrocarbons or H;
$R_2'$ represents an aliphatic substitution group with C1-20 hydrocarbons or H;
$R_2$ and $R_2'$ can be the same or different;
A chiral center is contained on the C atom attaching to $R_2$ and $R_2'$ when $R_2$ is different from $R_2'$, including when $R_2$ or $R_2'$ is a H atom; the configuration of the chiral center can be either (S) or (R);
$R_3$ represents an aliphatic substitution group with C1-20 hydrocarbons or H;
$R_4$ represents an aliphatic substitution group with C1-20 hydrocarbons or H;
$R_2$, $R_2'$, $R_3$ and $R_4$ may have one or multiple heteroatoms selected from F, Cl, N, O and S;
$R_2$ and $R_2'$ can be connected to form a 3 to 8 membered ring;
$R_3$ and $R_4$ can be connected to form a 3 to 8 membered ring;
$R_2$ or $R_2'$ can be connected to $R_3$ to form a 3 to 8 membered ring; and
$R_2$ or $R_2'$ can be connected to $R_4$ to form a 3 to 8 membered ring.

2. The compound of claim 1, or a pharmaceutically acceptable salt thereof, wherein $R_1$ may have one or multiple heteroatom substitutions selected from F and Cl.

3. The compound of claim 2, or a pharmaceutically acceptable salt thereof, wherein $R_2$ is one of the following substitution groups, Me, Et, iPr, Pr, cyclol Pr, and $R_2'$ is H.

4. The compound of claim 3, or a pharmaceutically acceptable salt thereof, wherein $R_3$ and $R_4$ are both H.

5. The compound of claim 3, or a pharmaceutically acceptable salt thereof, wherein the carbon atom to which $R_2$ and $R_2'$ are attached has a (S)-configuration.

6. The compound of claim 1, or a pharmaceutically acceptable salt thereof, said compound is
(S)-2-(1-aminopropyl)-6-(2-fluoropyridin-4-yl)thieno[3,2-d]pyrimidin-4(3H)-one (Compound 13a),
(S)-2-(1-amino-2-methylpropyl)-6-(2-chloropyridin-4-yl)thieno[3,2-d]pyrimidin-4(3H)-one (Compound 7a),
(S)-2-(1-amino-2-methylpropyl)-6-(piperazin-1-yl)thieno[3,2-d]pyrimidin-4(3H)-one (Compound 67),
(S)-2-(1-amino-2-methylpropyl)-6-(1H-pyrazol-3-yl)thieno[3,2-d]pyrimidin-4(3H)-one (Compound 7c),
(S)-2-(1-amino-2-methylpropyl)-6-(2-methylpyridin-4-yl)thieno[3,2-d]pyrimidin-4(3H)-one (Compound 7b),
(S)-2-(1-amino-2-methylpropyl)-6-(2,5-difluoropyridin-4-yl)thieno[3,2-d]pyrimidin-4(3H)-one (Compound 7d),
(S)-2-(1-amino-2-methylpropyl)-6-(isoxazol-4-yl)thieno[3,2-d]pyrimidin-4(3H)-one (Compound 7e),
(S)-2-(1-aminopropyl)-6-(3-fluoropyridin-4-yl)thieno[3,2-d]pyrimidin-4(3H)-one (Compound 13b),
(S)-2-(1-aminoethyl)-6-(3-fluoropyridin-4-yl)thieno[3,2-d]pyrimidin-4(3H)-one (Compound 21),
(S)-2-(amino(cyclopropyl)methyl)-6-(3-fluoropyridin-4-yl)thieno[3,2-d]pyrimidin-4(3H)-one (Compound 25),
(S)-6-(2-fluoropyridin-4-yl)-2-(2-methyl-1-(methylamino)propyl)thieno[3,2-d]pyrimidin-4(3H)-one (Compound 35),
2-(2-aminopropan-2-yl)-6-(2-fluoropyridin-4-yl)thieno[3,2-d]pyrimidin-4(3H)-one (Compound 39),
(S)-2-(1-amino-2-methylpropyl)-6-(1H-imidazol-4-yl)thieno[3,2-d]pyrimidin-4(3H)-one (Compound 45),
(S)-2-(1-amino-2-methylpropyl)-6-(pyridazin-4-yl)thieno[3,2-d]pyrimidin-4(3H)-one (Compound 49),
(S)-2-(1-amino-2-methylpropyl)-6-(pyrimidin-4-yl)thieno[3,2-d]pyrimidin-4(3H)-one (Compound 53),
(S)-2-(1-amino-2-methylpropyl)-6-(2H-1,2,3-triazol-4-yl)thieno[3,2-d]pyrimidin-4(3H)-one (Compound 58), or
(S)-2-(1-amino-2-methylpropyl)-6-(1H-pyrrol-3-yl)thieno[3,2-d]pyrimidin-4(3H)-one (Compound 65).

7. A pharmaceutical composition comprising a pharmaceutically acceptable carrier or diluent and a compound of claim 1 or a pharmaceutically acceptable salt thereof.

8. A method of treating CDC7 related diseases, the method comprising administering to a subject with an effective amount of a compound of claim 1.

* * * * *